(12) United States Patent
Chaplin et al.

(10) Patent No.: US 6,761,893 B2
(45) Date of Patent: Jul. 13, 2004

(54) MODIFIED VACCINIA ANKARA VIRUS VARIANT

(75) Inventors: Paul Chaplin, Munich (DE); **Paul How

Dose of MVA given in Prime and Boost (log)

A

B

MODIFIED VACCINIA ANKARA VIRUS VARIANT

The present invention provides an attenuated virus which is derived from Modified Vaccinia Ankara virus and which is characterized by the loss of its capability to reproductively replicate in human cell lines. It further describes recombinant viruses derived from this virus and the use of the virus or its recombinants as a medicament or vaccine. Additionally, a method is provided for inducing an immune response even in immune-compromised patients, patients with pre-existing immunity to the vaccine virus, or patients undergoing antiviral therapy.

BACKGROUND OF THE INVENTION

Modified Vaccinia Ankara (MVA) virus is related to vaccinia virus, a member of the genera Orthopoxvirus in the family of Poxviridae. MVA was generated by 516 serial passages on chicken embryo fibroblasts of the Ankara strain of vaccinia virus (CVA) (for review see Mayr, A., et al. Infection 3, 6–14 [1975]). As a consequence of these long-term passages, the resulting MVA virus deleted about 31 kilobases of its genomic sequence and, therefore, was described as highly host cell restricted to avian cells (Meyer, H. et al., J. Gen. Virol. 72, 1031–1038 [1991]). It was shown in a variety of animal models that the resulting MVA was significantly avirulent (Mayr, A. & Danner, K. [1978] Dev. Biol. Stand. 41: 225–34). Additionally, this MVA strain has been tested in clinical trials as a vaccine to immunize against the human smallpox disease (Mayr et al., Zbl. Bakt. Hyg. I, Abt. Org. B 167, 375–390 [1987], Stickl et al., Dtsch. med. Wschr. 99, 2386–2392 [1974]). These studies involved over 120,000 humans, including high-risk patients, and proved that compared to vaccinia based vaccines, MVA had diminished virulence or infectiousness while it induced a good specific immune response.

In the following decades, MVA was engineered for use as a viral vector for recombinant gene expression or as a recombinant vaccine (Sutter, G. et al. [1994], Vaccine 12: 1032–40).

In this respect, it is most astonishing that even though Mayr et al. demonstrated during the 1970s that MVA is highly attenuated and avirulent in humans and mammals, some recently reported observations (Blanchard et al., 1998, J Gen Virol 79, 1159–1167; Carroll & Moss, 1997, Virology 238, 198–211; Altenberger, U.S. Pat. No. 5,185,146; Ambrosini et al., 1999, J Neurosci Res 55(5), 569) have shown that MVA is not fully attenuated in mammalian and human cell lines since residual replication might occur in these cells. It is assumed that the results reported in these publications have been obtained with various known strains of MVA since the viruses used essentially differ in their properties, particularly in their growth behavior in various cell lines.

Growth behavior is recognized as an indicator for virus attenuation. Generally, a virus strain is regarded as attenuated if it has lost its capacity or only has reduced capacity to reproductively replicate in host cells. The above-mentioned observation, that MVA is not completely replication incompetent in human and mammalian cells, brings into question the absolute safety of known MVA as a human vaccine or a vector for recombinant vaccines.

Particularly for a vaccine, as well as for a recombinant vaccine, the balance between the efficacy and the safety of the vaccine vector virus is extremely important.

OBJECT OF THE INVENTION

Thus, an object of the invention is to provide novel virus strains having enhanced safety for the development of safer products, such as vaccines or pharmaceuticals. Moreover, a further object is to provide a means for improving an existing vaccination regimen.

DETAILED DESCRIPTION OF THE INVENTION

To achieve the foregoing objectives, according to a preferred embodiment of the present invention, new vaccinia viruses are provided which are capable of reproductive replication in non-human cells and cell lines, especially in chicken embryo fibroblasts (CEF), but not capable of reproductive replication in a human cell line known to permit replication with known vaccinia strains.

Known vaccinia strains reproductively replicate in at least some human cell lines, in particular the human keratinocyte cell line HaCat (Boukamp et al. 1988, J Cell Biol 106(3): 761–71). Replication in the HaCat cell line is predictive for replication in vivo, in particular for in vivo replication in humans. It is demonstrated in the example section that all known vaccinia strains tested that show a residual reproductive replication in HaCat also replicate in vivo. Thus, the invention preferably relates to vaccinia viruses that do not reproductively replicate in the human cell line HaCat. Most preferably, the invention concerns vaccinia virus strains that are not capable of reproductive replication in any of the following human cell lines: human cervix adenocarcinoma cell line HeLa (ATCC No. CCL-2), human embryo kidney cell line 293 (ECACC No. 85120602), human bone osteosarcoma cell line 143B (ECACC No. 91112502) and the HaCat cell line.

The growth behaviour or amplification/replication of a virus is normally expressed by the ratio of virus produced from an infected cell (Output) to the amount originally used to infect the cell in the first place (Input) ("amplification ratio"). A ratio of "1" between Output and Input defines an amplification status wherein the amount of virus produced from the infected cells is the same as the amount initially used to infect the cells. This ratio is understood to mean that the infected cells are permissive for virus infection and virus reproduction.

An amplification ratio of less than 1, i.e., a decrease of the amplification below input level, indicates a lack of reproductive replication and thus, attenuation of the virus. Therefore, it was of particular interest for the inventors to identify and isolate a strain that exhibits an amplification ratio of less than 1 in several human cell lines, in particular all of the human cell lines 143B, HeLa, 293, and HaCat.

Thus, the term "not capable of reproductive replication" means that the virus of the present invention exhibits an amplification ratio of less than 1 in human cell lines, such as 293 (ECACC No. 85120602), 143B (ECACC No. 91112502), HeLa (ATCC No. CCL-2) and HaCat (Boukamp et al. 1988, J Cell Biol 106(3): 761–71) under the conditions outlined in Example 1 of the present specification. Preferably, the amplification ratio of the virus of the invention is 0.8 or less in each of the above human cell lines, i.e., HeLa, HaCat, and 143B.

Viruses of the invention are demonstrated in Example 1 and Table 1 not to reproductively replicate in cell lines 143B, HeLa and HaCat. The particular strain of the invention that has been used in the examples was deposited on Aug. 30, 2000 at the European Collection of Cell Cultures (ECACC) under number V00083008. This strain is referred to as "MVA-BN" throughout the Specification. It has already been noted that the known MVA strains show residual replication in at least one of the human cell lines tested (FIG.

1, Example 1). All known vaccinia strains show at least some replication in the cell line HaCat, whereas the MVA strains of the invention, in particular MVA-BN, do not reproductively replicate in HaCat cells. In particular, MVA-BN exhibits an amplification ratio of 0.05 to 0.2 in the human embryo kidney cell line 293 (ECACC No. 85120602). In the human bone osteosarcoma cell line 143B (ECACC No. 91112502), the ratio is in the range of 0.0 to 0.6. For the human cervix adenocarcinoma cell line HeLa (ATCC No. CCL-2) and the human keratinocyte cell line HaCat (Boukamp et al. 1988, J Cell Biol 106(3): 761–71), the amplification ratio is in the range of 0.04 to 0.8 and of 0.02 to 0.8, respectively. MVA-BN has an amplification ratio of 0.01 to 0.06 in African green monkey kidney cells (CV1: ATCC No. CCL-70). Thus, MVA-BN, which is a representative strain of the invention, does not reproductively replicate in any of the human cell lines tested.

The amplification ratio of MVA-BN is clearly above 1 in chicken embryo fibroblasts (CEF: primary cultures). As outlined above, a ratio of more than "1" indicates reproductive replication since the amount of virus produced from the infected cells is increased compared to the amount of virus that was used to infect the cells. Therefore, the virus can be easily propagated and amplified in CEF primary cultures with a ratio above 500.

In a particular embodiment of the present invention, the invention concerns derivatives of the virus as deposited under ECACC V0083008. "Derivatives" of the viruses as deposited under ECACC V00083008 refer to viruses exhibiting essentially the same replication characteristics as the deposited strain but exhibiting differences in one or more parts of its genome. Viruses having the same "replication characteristics" as the deposited virus are viruses that replicate with similar amplification ratios as the deposited strain in CEF cells and the cell lines HeLa, HaCat and 143B; and that show a similar replication in vivo, as determined in the AGR129 transgenic mouse model (see below).

In a further preferred embodiment, the vaccinia virus strains of the invention, in particular MVA-BN and its derivatives, are characterized by a failure to replicate in vivo. In the context of the present invention, "failure to replicate in vivo" refers to viruses that do not replicate in humans and in the mouse model described below. The "failure to replicate in vivo" can be preferably determined in mice that are incapable of producing mature B and T cells. An example of such mice is the transgenic mouse model AGR129 (obtained from Mark Sutter, Institute of Virology, University of Zurich, Zurich, Switzerland). This mouse strain has targeted gene disruptions in the IFN receptor type I (IFN-α/β) and type II (IFN-γ) genes, and in RAG. Due to these disruptions, the mice have no IFN system and are incapable of producing mature B and T cells, and as such, are severely immune-compromised and highly susceptible to a replicating virus. In addition to the AGR129 mice, any other mouse strain can be used that is incapable of producing mature B and T cells, and as such, is severely immune-compromised and highly susceptible to a replicating virus. In particular, the viruses of the present invention do not kill AGR129 mice within a time period of at least 45 days, more preferably within at least 60 days, and most preferably within 90 days post infection of the mice with $10^7$ pfu virus administered via intra-peritoneal injection. Preferably, the viruses that exhibit "failure to replicate in vivo" are further characterized in that no virus can be recovered from organs or tissues of the AGR129 mice 45 days, preferably 60 days, and most preferably 90 days after infection of the mice with $10^7$ pfu virus administered via intra-peritoneal injection. Detailed information regarding the infection assays using AGR129 mice and the assays used to determine whether virus can be recovered from organs and tissues of infected mice can be found in the example section.

In a further preferred embodiment, the vaccinia virus strains of the invention, in particular MVA-BN and its derivatives, are characterized as inducing a higher specific immune response compared to the strain MVA 575, as determined in a lethal challenge mouse model. Details of this experiment are outlined in Example 2, shown below. Briefly, in such a model unvaccinated mice die after infection with replication competent vaccinia strains such as the Western Reserve strain L929 TK+ or IHD-J. Infection with replication competent vaccinia viruses is referred to as "challenge" in the context of description of the lethal challenge model. Four days after the challenge, the mice are usually killed and the viral titer in the ovaries is determined by standard plaque assays using VERO cells (for more details see example section). The viral titer is determined for unvaccinated mice and for mice vaccinated with vaccina viruses of the present invention. More specifically, the viruses of the present invention are characterized in that, in this test after the vaccination with $10^2$ TCID$_{50}$/ml of virus of the present invention, the ovarian virus titers are reduced by at least 70%, preferably by at least 80%, and more preferably by at least 90%, compared to unvaccinated mice.

In a further preferred embodiment, the vaccinia viruses of the present invention, in particular MVA-BN and its derivatives, are useful for immunization with prime/boost administration of the vaccine. There have been numerous reports suggesting that prime/boost regimes using a known MVA as a delivery vector induce poor immune responses and are inferior to DNA-prime/MVA-boost regimes (Schneider et al., 1998, Nat. Med. 4; 397–402). In all of those studies the MVA strains that have been used are different from the vaccinia viruses of the present invention. To explain the poor immune response if MVA was used for prime and boost administration it has been hypothesized that antibodies generated to MVA during the prime-administration neutralize the MVA administered in the second immunization, thereby preventing an effective boost of the immune response. In contrast, DNA-prime/MVA-boost regimes are reported to be superior at generating high avidity responses because this regime combines the ability of DNA to effectively prime the immune response with the properties of MVA to boost the response in the absence of a pre-existing immunity to MVA. Clearly, if a pre-existing immunity to MVA and/or vaccinia prevents boosting of the immune response, then the use of MVA as a vaccine or therapeutic would have limited efficacy, particularly in the individuals that have been previously vaccinated against smallpox. However, according to a further embodiment, the vaccinia virus of the present invention, in particular MVA-BN and its derivatives, as well as corresponding recombinant viruses harboring heterologous sequences, can be used to efficiently first prime and then boost immune responses in naive animals, as well as animals with a pre-existing immunity to poxviruses. Thus, the vaccinia virus of the present invention induces at least substantially the same level of immunity in vaccinia virus prime/vaccinia virus boost regimes compared to DNA-prime/vaccinia virus boost regimes. The term "animal" as used in the present description is intended to also include human beings. Thus, the virus of the present invention is also useful for prime/boost regimes in human beings. If the virus is a non-recombinant virus such as MVA-BN or a derivative thereof, the virus may be used as a smallpox vaccine in humans, wherein the same virus can be used in both the priming and boosting vaccination. If the virus is a recombinant virus such as MVA-BN or a derivative thereof that encodes a heterologous antigen, the virus may be used in humans as a vaccine against the agent from which the heterologous antigen is derived, wherein the same virus can be used in both the priming and boosting vaccination.

A vaccinia virus is regarded as inducing at least substantially the same level of immunity in vaccinia virus prime/vaccinia virus boost regimes if, when compared to DNA-prime/vaccinia virus boost regimes, the CTL response, as measured in one of the following two assays ("assay 1" and "assay 2"), preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both of the following assays.

Assay 1

For vaccinia virus prime/vaccinia virus boost administrations, 6–8 week old BALB/c (H-2d) mice are prime-immunized by intravenous administration with $10^7$ $TCID_{50}$ vaccinia virus of the invention expressing the murine polytope as described in Thomson et al., 1988, J. Immunol. 160, 1717 and then boost-immunized with the same amount of the same virus, administered in the same manner three weeks later. To this end, it is necessary to construct a recombinant vaccinia virus expressing the polytope. Methods to construct such recombinant viruses are known to a person skilled in the art and are described in more detail below. In DNA prime/vaccinia virus boost regimes the prime vaccination is done by intra muscular injection of the mice with 50 $\mu$g DNA expressing the same antigen as the vaccinia virus. The boost administration with the vaccinia virus is done in exactly the same way as for the vaccinia virus prime/vaccinia virus boost administration. The DNA plasmid expressing the polytope is also described in the publication referenced above, i.e., Thomson, et al. In both regimes, the development of a CTL response against the epitopes is determined two weeks after the boost administration. The determination of the CTL response is preferably done using the ELISPOT analysis as described by Schneider, et al., 1998, Nat. Med. 4, 397–402, and as outlined in the examples section below for a specific virus of the invention. The virus of the invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-$\gamma$ producing cells/$10^6$ spleen cells (see also experimental section).

Assay 2

This assay basically corresponds to assay 1. However, instead of using $10^7$ $TCID_{50}$ vaccinia virus administered i.v., as in Assay 1; in Assay 2, $10^8$ $TCID_{50}$ vaccinia virus of the present invention is administered by subcutaneous injection for both prime and boost immunization. The virus of the present invention is characterized in this experiment in that the CTL immune response against the epitopes mentioned above, which is induced by the vaccinia virus prime/vaccinia virus boost administration, is substantially the same, preferably at least the same, as that induced by DNA prime/vaccinia virus boost administration, as assessed by the number of IFN-$\gamma$ producing cells/$10^6$ spleen cells (see also experimental section).

The strength of a CTL response as measured in one of the assays shown above corresponds to the level of protection.

Thus, the viruses of the present invention are particularly suitable for vaccination purposes.

In summary, a representative vaccinia virus of the present invention is characterized by having at least one of the following properties:
  (i) capability of reproductive replication in chicken embryo fibroblasts (CEF), but no capability of reproductive replication in a human cell line known to permit replication with known vaccinia strains,
  (ii) failure to replicate in vivo in those animals, including humans, in which the virus is used as a vaccine or active ingredient of a pharmaceutical composition,
  (iii) induction of a higher specific immune response compared to a known vaccinia strain and/or
  (iv) induction of at least substantially the same level of a specific immune response in vaccinia virus prime/vaccinia virus boost regimes when compared to DNA-prime/vaccinia virus boost regimes.

Preferably, the vaccinia virus of the present invention has at least two of the above properties, and more preferably at least three of the above properties. Most preferred are vaccinia viruses having all of the above properties.

Representative vaccinia virus strains are MVA 575 deposited on Dec. 7, 2000 at the European Collection of Animal Cell Cultures (ECACC) with the deposition number V00120707; and MVA-BN, deposited on Aug. 30, 2000, at ECACC with the deposition number V000083008, and derivatives thereof, in particular if it is intended to vaccinate/treat humans. MVA-BN and its derivatives are most preferred for humans.

In a further embodiment, the invention concerns a kit for vaccination comprising a virus of the present invention for the first vaccination ("priming") in a first vial/container and for a second vaccination ("boosting") in a second vial/container. The virus may be a non-recombinant vaccinia virus, i.e., a vaccinia virus that does not contain heterologous nucleotide sequences. An example of such a vaccinia virus is MVA-BN and its derivatives. Alternatively, the virus may be a recombinant vaccinia virus that contains additional nucleotide sequences that are heterologous to the vaccinia virus. As outlined in other sections of the description, the heterologous sequences may code for epitopes that induce a response by the immune system. Thus, it is possible to use the recombinant vaccinia virus to vaccinate against the proteins or agents comprising the epitope. The viruses may be formulated as shown below in more detail. The amount of virus that may be used for each vaccination has been defined above.

A process to obtain a virus of the instant invention may comprise the following steps:
  (i) introducing a vaccinia virus strain, preferably MVA 574 or MVA 575 (ECACC V00120707) into non-human cells in which the virus is able to reproductively replicate, wherein the non-human cells are preferably selected from CEF cells,
  (ii) isolating/enriching virus particles from these cells and
  (iii) analyzing whether the obtained virus has at least one of the desired biological properties as previously defined above,
wherein the above steps can optionally be repeated until a virus with the desired replication characteristics is obtained. The invention further relates to the viruses obtained by the method of the instant invention. Methods for determining the expression of the desired biological properties are explained in other parts of this description.

In applying this method, the inventors identified and isolated in several rounds of clone purification a strain of the present invention starting with the MVA isolate passage 575 (MVA 575). This new strain corresponds to the strain with the accession number ECACC V0083008, mentioned above.

The growth behavior of the vaccinia viruses of the present invention, in particular the growth behavior of MVA-BN, indicates that the strains of the present invention are far superior to any other characterized MVA isolates in terms of attenuation in human cell lines and failure to replicate in vivo. The strains of the present invention are therefore ideal candidates for the development of safer products such as vaccines or pharmaceuticals, as described below.

In one further embodiment, the virus of the present invention, in particular MVA-BN and its derivatives, is used as a vaccine against human poxvirus diseases, such as smallpox.

In a further embodiment, the virus of the present invention may be recombinant, i.e., may express heterologous genes as, e.g., antigens or epitopes heterologous to the virus, and may thus be useful as a vaccine to induce an immune response against heterologous antigens or epitopes.

The term "immune response" means the reaction of the immune system when a foreign substance or microorganism enters the organism. By definition, the immune response is divided into a specific and an unspecific reaction although both are closely related. The unspecific immune response is the immediate defense against a wide variety of foreign substances and infectious agents. The specific immune response is the defense raised after a lag phase, when the organism is challenged with a substance for the first time. The specific immune response is highly efficient and is responsible for the fact that an individual who recovers from a specific infection is protected against this specific infection. Thus, a second infection with the same or a very similar infectious agent causes much milder symptoms or no symptoms at all, since there is already a "pre-existing immunity" to this agent. Such immunity and immunological memory persist for a long time, in some cases even lifelong. Accordingly, the induction of an immunological memory can be used for vaccination.

The "immune system" means a complex organ involved in the defense of the organism against foreign substances and microorganisms. The immune system comprises a cellular component, comprising several cell types, such as, e.g., lymphocytes and other cells derived from white blood cells, and a humoral component, comprising small peptides and complement factors.

"Vaccination" means that an organism is challenged with an infectious agent, e.g., an attenuated or inactivated form of the infectious agent, to induce a specific immunity. The term vaccination also covers the challenge of an organism with recombinant vaccinia viruses of the present invention, in particular recombinant MVA-BN and its derivatives, expressing antigens or epitopes that are heterologous to the virus. Examples of such epitopes are provided elsewhere in the description and include e.g., epitopes from proteins derived from other viruses, such as the Dengue virus, Hepatitis C virus, HIV, or epitopes derived from proteins that are associated with the development of tumors and cancer. Following administration of the recombinant vaccinia virus, the epitopes are expressed and presented to the immune system. A specific immune response against these epitopes may be induced. The organism, thus, is immunized against the agent/protein containing the epitope that is encoded by the recombinant vaccinia virus.

"Immunity" means partial or complete protection of an organism against diseases caused by an infectious agent due to a successful elimination of a preceding infection with the infectious agent or a characteristic part thereof. Immunity is based on the existence, induction, and activation of specialized cells of the immune system.

As indicated above, in one embodiment of the invention the recombinant viruses of the present invention, in particular recombinant MVA-BN and its derivatives, contain at least one heterologous nucleic acid sequence. The term "heterologous" is used hereinafter for any combination of nucleic acid sequences that is not normally found intimately associated with the virus in nature; such virus is also called a "recombinant virus".

According to a further embodiment of the present invention, the heterologous sequences are preferably antigenic epitopes that are selected from any non-vaccinia source. Most preferably, the recombinant virus expresses one or more antigenic epitopes from: *Plasmodium falciparum*, mycobacteria, influenza virus, viruses of the family of flaviviruses, paramyxoviruses, hepatitis viruses, human immunodeficiency viruses, or from viruses causing hemorrhagic fever, such as hantaviruses or filoviruses, i.e., ebola or marburg virus.

According to still a further embodiment, but also in addition to the above-mentioned selection of antigenic epitopes, the heterologous sequences can be selected from another poxviral or a vaccinia source. These viral sequences can be used to modify the host spectrum or the immunogenicity of the virus.

In a further embodiment the virus of the present invention may code for a heterologous gene/nucleic acid expressing a therapeutic compound. A "therapeutic compound" encoded by the heterologous nucleic acid in the virus can be, e.g., a therapeutic nucleic acid, such as an antisense nucleic acid or a peptide or protein with desired biological activity.

According to a further preferred embodiment, the expression of a heterologous nucleic acid sequence is preferably, but not exclusively, under the transcriptional control of a poxvirus promoter, more preferably of a vaccinia virus promoter.

According to still a further embodiment, the heterologous nucleic acid sequence is preferably inserted into a non-essential region of the virus genome. In another preferred embodiment of the invention, the heterologous nucleic acid sequence is inserted at a naturally occurring deletion site of the MVA genome as disclosed in PCT/EP96/02926. Methods for inserting heterologous sequences into the poxviral genome are known to a person skilled in the art.

According to yet another preferred embodiment, the invention also includes the genome of the virus, its recombinants, or functional parts thereof. Such viral sequences can be used to identify or isolate the virus or its recombinants, e.g., by using PCR, hybridization technologies, or by establishing ELISA assays. Furthermore, such viral sequences can be expressed from an expression vector to produce the encoded protein or peptide that then may supplement deletion mutants of a virus that lacks the viral sequence contained in the expression vector.

"Functional part" of the viral genome means a part of the complete genomic sequence that encodes a physical entity, such as a protein, protein domain, or an epitope of a protein. Functional part of the viral genome also describes parts of the complete genomic sequence that code for regulatory elements or parts of such elements with individualized activity, such as promoter, enhancer, cis- or trans-acting elements.

The recombinant virus of the present invention may be used for the introduction of a heterologous nucleic acid sequence into a target cell, the sequence being either homologous or heterologous to the target cell. The introduction of a heterologous nucleic acid sequence into a target cell may be used to produce in vitro heterologous peptides or polypeptides, and/or complete viruses encoded by the sequence. This method comprises the infection of a host cell with the recombinant MVA; cultivation of the infected host cell under suitable conditions; and isolation and/or enrichment of the peptide, protein and/or virus produced by the host cell.

Furthermore, the method for introduction of a homologous or heterologous sequence into cells may be applied for in vitro and preferably in vivo therapy. For in vitro therapy, isolated cells that have been previously (ex vivo) infected with the virus are administered to a living animal body for inducing an immune response. For in vivo therapy, the virus or its recombinants are directly administered to a living animal body to induce an immune response. In this case, the cells surrounding the site of inoculation are directly infected in vivo by the virus, or its recombinants, of the present invention.

Since the virus of the invention is highly growth restricted in human and monkey cells and thus, highly attenuated, it is ideal to treat a wide range of mammals, including humans. Hence, the present invention also provides a pharmaceutical composition and a vaccine, e.g., for inducing an immune response in a living animal body, including a human. The virus of the invention is also safe in any other gene therapy protocol.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the virus or a recombinant of the present invention, is converted into a physiologically acceptable form. This can be done based on experience in the preparation of poxvirus vaccines used for vaccination against smallpox (as described by Stickl, H. et al. [1974] Dtsch. med. Wschr. 99, 2386–2392). For example, the purified virus is stored at −80° C. with a titre of $5\times10^8$ $TCID_{50}$/ml formulated in about 10 mM Tris, 140 mM NaCl, pH 7.4. For the preparation of vaccine shots, e.g., $10^2$–$10^8$ particles of the virus are lyophilized in 100 ml of phosphate-buffered saline (PBS) in the presence of 2% peptone and 1% human albumin in an ampoule, preferably a glass ampoule. Alternatively, the vaccine shots can be produced by stepwise, freeze-drying of the virus in a formulation. This formulation can contain additional additives such as mannitol, dextran, sugar, glycine, lactose, polyvinylpyrrolidone, or other additives, such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in 0.1 to 0.5 ml of an aqueous solution, preferably physiological saline or Tris buffer, and administered either systemically or locally, i.e., by parenteral, intramuscular, or any other path of administration know to a skilled practitioner. The mode of administration, dose, and number of administrations can be optimized by those skilled in the art in a known manner.

Additionally according to a further embodiment, the virus of the present invention is particularly useful to induce immune responses in immune-compromised animals, e.g., monkeys (CD4<$400/\mu l$ of blood) infected with SIV, or immune-compromised humans. The term "immune-compromised" describes the status of the immune system of an individual that exhibits only incomplete immune responses or has a reduced efficiency in the defense against infectious agents. Even more interesting and according to still a further embodiment, the virus of the present invention can boost immune responses in immune-compromised animals or humans even in the presence of a pre-existing immunity to poxvirus in these animals or humans. Of particular interest, the virus of the present invention can also boost immune responses in animals or humans receiving an antiviral, e.g., antiretroviral therapy. "Antiviral therapy" includes therapeutic concepts in order to eliminate or suppress viral infection including, e.g., (i) the administration of nucleotide analogs, (ii) the administration of inhibitors for viral enzymatic activity or viral assembling, or (iii) the administration of cytokines to influence immune responses of the host.

According to still a further embodiment, the vaccine is especially, but not exclusively, applicable in the veterinary field, e.g., immunization against animal pox infection. In small animals, the immunizing inoculation is preferably administered by nasal or parenteral administration, whereas in larger animals or humans, a subcutaneous, oral, or intramuscular inoculation is preferred.

The inventors have found that a vaccine shot containing an effective dose of only $10^2$ $TCID_{50}$ (tissue culture infectious dose) of the virus of the present invention is sufficient to induce complete immunity against a wild type vaccinia virus challenge in mice. This is particularly surprising since such a high degree of attenuation of the virus of the present invention would be expected to negatively influence and thereby, reduce its immunogenicity. Such expectation is based on the understanding that for induction of an immune response, the antigenic epitopes must be presented to the immune system in sufficient quantity. A virus that is highly attenuated and thus, not replicating, can only present a very small amount of antigenic epitopes, i.e., as much as the virus itself incorporates. The amount of antigen carried by viral particles is not considered to be sufficient for induction of a potent immune response. However, the virus of the invention stimulates, even with a very low effective dose of only $10^2$ $TCID_{50}$, a potent and protective immune response in a mouse/vaccinia challenge model. Thus, the virus of the present invention exhibits an unexpected and increased induction of specific immunity compared to other characterized MVA strains. This makes the virus of the present invention and any vaccine derived thereof, especially useful for application in immune-compromised animals or humans.

According to still another embodiment of the invention, the virus is used as an adjuvant. An "adjuvant" in the context of the present description refers to an enhancer of the specific immune response in vaccines. "Using the virus as adjuvant" means including the virus in a pre-existing vaccine to additionally stimulate the immune system of the patient who receives the vaccine. The immunizing effect of an antigenic epitope in most vaccines is often enhanced by the addition of a so-called adjuvant. An adjuvant co-stimulates the immune system by causing a stronger specific immune reaction against an antigenic epitope of a vaccine. This stimulation can be regulated by factors of the unspecific immune system, such as interferon and interleukin. Hence, in a further embodiment of the invention, the virus is used in mammals, including humans, to activate, support, or suppress the immune system, and preferably to activate the immune response against any antigenic determinant. The virus may also be used to support the immune system in a situation of increased susceptibility to infection, such as in the case of stress.

The virus used as an adjuvant may be a non-recombinant virus, i.e., a virus that does not contain heterologous DNA in its genome. An example of this type of virus is MVA-BN. Alternatively, the virus used as an adjuvant is a recombinant virus containing in its genome heterologous DNA sequences that are not naturally present in the viral genome. For use as an adjuvant, the recombinant viral DNA preferably contains and expresses genes that code for immune stimulatory peptides or proteins such as interleukins.

According to a further embodiment, it is preferred that the virus is inactivated when used as an adjuvant or added to another vaccine. The inactivation of the virus may be performed by e.g., heat or chemicals, as known in the art.

Preferably, the virus is inactivated by β-propriolacton. According to this embodiment of the invention, the inactivated virus may be added to vaccines against numerous infectious or proliferative diseases to increase the immune response of the patient to this disease.

SUMMARY OF THE INVENTION

The invention inter alia comprises the following, alone or in combination:

A method for inducing a specific immune response in a living animal body, including a human, comprising administering an amount of a vaccinia preparation which includes an effective amount of a vaccinia virus having at least one of the following advantageous properties:
- capability of reproductive replication in vitro in chicken embryo fibroblasts (CEF), but no capability of reproductive replication in a human cell line known to permit replication with known vaccinia strains,
- failure to replicate in vivo in those animals including humans in which the virus is used as a vaccine or active ingredient of a pharmaceutical composition,
- induction of a higher specific immune response compared to a known vaccinia strain, and/or
- induction of at least the same level of a specific immune response in vaccinia virus prime/vaccinia virus boost regimes when compared to DNA-prime/vaccinia virus boost regimes, wherein the preparation is administered in therapeutically effective amounts in a first inoculation or "priming inoculation" and in a second inoculation or "boosting inoculation",
such a method, wherein the vaccinia virus has at least two (2) of the advantageous properties,
such a method, wherein the vaccinia virus has at least three (3) of the advantageous properties,
such a method, wherein the vaccinia virus has all four (4) of the advantageous properties,
such a method, wherein the vaccinia virus is not capable of reproductive replication in the human keratinocyte cell line (HaCat),
such a method, wherein the vaccinia virus is not capable of reproductive replication in any of the following human cell lines: the human keratinocyte cell line (HaCat), the human embryo kidney cell line (293), the human bone osteosarcoma cell line (143B), and the human cervix adenocarcinoma cell line (HeLa),
such a method, wherein the vaccinia virus is capable of a replication amplification ratio of greater than 500 in CEF cells,
such a method, wherein the vaccinia virus is not capable of replication in mammals,
such a method, wherein the vaccinia virus is not capable of replication in humans,
such a method, wherein the known vaccinia strain is a Modified Vaccinia Ankara virus (MVA),
such a method, wherein the known vaccinia strain is MVA 572,
such a method, wherein the known vaccinia strain is MVA 575,
such a method, in which the vaccinia virus is that virus deposited at the European Collection of Cell Cultures (ECACC), Salisbury (UK) under number V00083008 and derivatives thereof,
such a method, wherein the vaccinia virus is monoclonal,
such a method, wherein the vaccinia virus is not capable of replicating in immune compromised animals, including humans,
such a method, wherein the vaccinia virus comprises at least one heterologous nucleic acid sequence,
such a method, wherein the vaccinia virus comprises a heterologous nucleic acid sequence selected from a sequence coding for at least one antigen, antigenic epitope, or a therapeutic compound,
such a method, wherein the specific immune response is directed to the vaccinia virus,
such a method, wherein the specific immune response is directed to heterologous material encoded in the vaccinia virus,
such a method, wherein the specific immune response is directed to HIV,
such a method, wherein the specific immune response is two (2) fold,
such a method, wherein the specific immune response is a specific immunity to an orthopox,
such a method, wherein the specific immune response is a specific immunity to smallpox,
such a method, comprising the administration of at least $10^2$ tissue culture infectious dose (TCID$_{50}$) of the vaccinia virus,
such a method, comprising the administration of a genome or functional parts of the vaccinia virus, to induce a specific immune response,
such a method, wherein the vaccinia virus, genome, or functional part thereof, is administered as adjuvant.

A vaccinia virus having at least one of the following properties:
- capability of reproductive replication in chicken embryo fibroblasts (CEF), but no capability of reproductive replication in the human cell line HaCat,
- failure to replicate in vivo, in those animals, including humans, in which the virus is used as a vaccine or active ingredient of a pharmaceutical composition,
- induction of a higher specific immune response compared to the strain MVA 575 (ECACC V00120707) in a lethal challenge model and/or
- induction of at least substantially the same level of immunity in vaccinia virus prime/vaccinia virus boost regimes when compared to DNA-prime/vaccinia virus boost regimes.

The virus as above, wherein the virus is not capable of reproductively replicating in any of the following human cell lines: the human embryo kidney cell line 293, the human bone osteosarcoma cell line 143B and the human cervix adenocarcinoma cell line HeLa.

The virus as above, being deposited at the European Collection of Cell Cultures (ECACC), Salisbury (UK) under number V00083008 and derivatives thereof.

The virus as above, comprising at least one heterologous nucleic acid sequence.

The virus as above, wherein the heterologous nucleic acid sequence is a sequence coding for at least one antigen, antigenic epitope, and/or a therapeutic compound.

A genome or functional parts thereof derived from the virus as defined above.

A pharmaceutical composition comprising the virus as above, and/or the genome and/or functional part thereof as defined above, and a pharmaceutically acceptable carrier, diluent and/or additive.

A vaccine comprising the virus as above, and/or the genome and/or functional part thereof, as defined above.

The virus as above, the genome and/or functional part thereof as defined above, the composition as defined above or the vaccine as defined above as a medicament for affecting, preferably inducing, an immune response in a living animal, including a human.

The virus as above, the pharmaceutical composition as defined above, the vaccine as defined above or the virus as defined above, wherein the virus, the composition or the vaccine is administered in therapeutically effective amounts in a first inoculation ("priming inoculation") and in a second inoculation ("boosting inoculation").

The use of the virus as above, and/or the genome as defined above, for the preparation of a medicament or a vaccine.

A method for introducing homologous and/or heterologous nucleic acid sequences into target cells comprising the infection of the target cells with the virus comprising heterologous sequences as defined above, or the transfection of the target cell with the genome as defined above.

A method for producing a peptide, protein and/or virus comprising

Infection of a host cell with the virus as above,

Cultivation of the infected host cell under suitable conditions, and

Isolation and/or enrichment of the peptide and/or protein and/or viruses produced by said host cell.

A method for affecting, preferably inducing an immune response in a living animal body, including a human, comprising administering the virus as above, the genome and/or functional part thereof as defined above, the composition as defined above or the vaccine as defined above to the animal or human to be treated.

The method as above, comprising the administration of at least $10^2$ TCID$_{50}$ (tissue culture infectious dose) of the virus.

The method as above, wherein the virus, the composition, or the vaccine is administered in therapeutically effective amounts in a first inoculation ("priming inoculation") and in a second inoculation ("boosting inoculation").

The method as above, wherein the animal is immune-compromised.

The method as above, wherein the animal has a pre-existing immunity to poxviruses.

The method as above, wherein the animal is undergoing an antiviral therapy.

The method wherein the animal is undergoing an antiviral therapy, characterized in that the antiviral therapy is an antiretroviral therapy The use of the virus as above, the genome and/or functional part thereof as defined above, as an adjuvant.

A method for enhancing a specific immune response against an antigen and/or an antigenic epitope included in a vaccine, comprising administration of the virus as above or the genome as defined above, as an adjuvant to a living animal body including a human to be treated with the vaccine.

The virus as above or the genome as defined above, as adjuvant.

A cell, preferably a human cell containing the virus as above or the genome or functional part thereof as defined above.

A method for obtaining the vaccinia virus as above comprising the following steps:

introducing a vaccinia virus strain, preferably MVA 575 into non human cells in which the virus is able to reproductively replicate, wherein the non-human cells are preferably selected from CEF cells, isolating/enriching virus particles from these cells and analyzing whether the obtained virus has at least one of the biological properties as defined above, wherein the above steps can optionally be repeated until a virus with the desired replication characteristics is obtained A kit for prime/boost immunization comprising a virus as above, a vaccine as above, or the virus as drug as defined above for a first inoculation ("priming inoculation") in a first vial/container and for a second inoculation ("boosting inoculation") in a second vial/container.

The use of the virus as above, the composition as defined above and/or of the vaccine as defined above, for the preparation of a vaccine wherein the virus, the composition or the vaccine is administered in a prime inoculation and wherein the same virus or vaccine is administered in a boost inoculation.

EXAMPLES

Figure 1A:
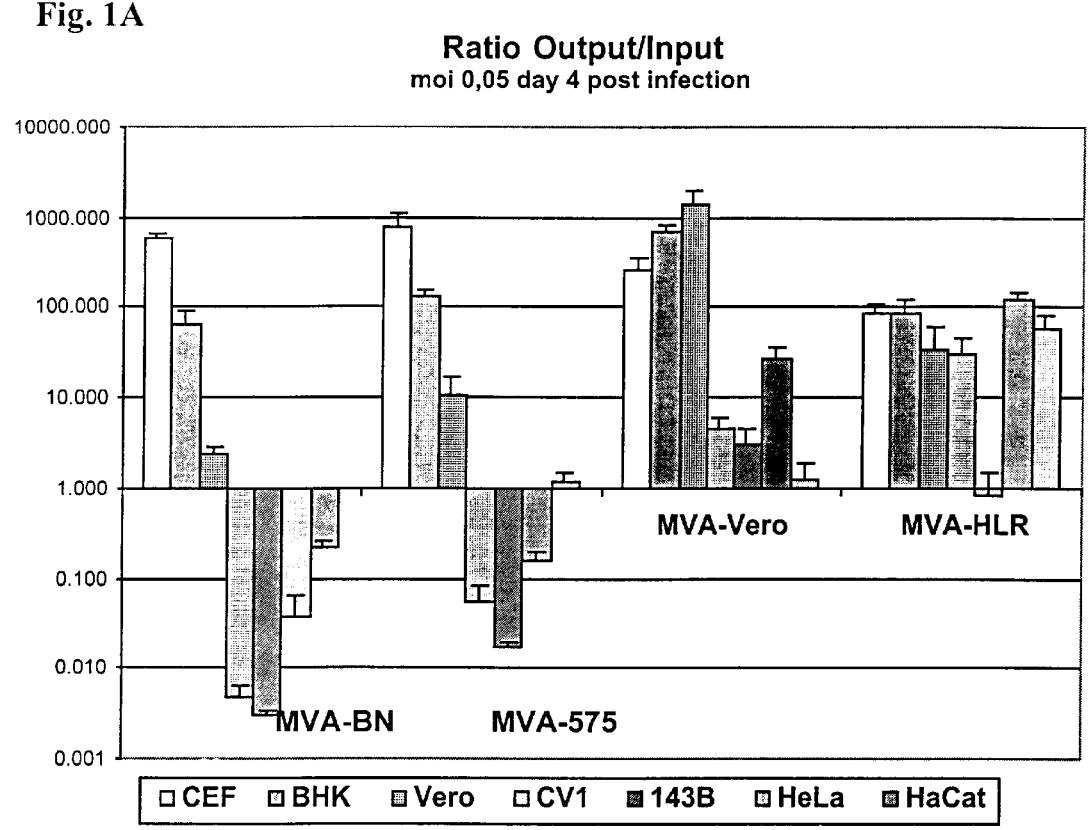
FIG. 1: Growth kinetics of different strains of MVA in different cell lines. In 1A, the results are grouped according to the MVA strains tested; whereas in 1B, the results are grouped according to the cell lines tested. In 1B, the amount of virus recovered from a cell line after four days (D4) of culture was determined by plaque assay and expressed as the ratio of virus recovered after 4 days to the initial inoculum on day 1 (D1).

The following examples further illustrate the present invention. It should be understood by a person skilled in the art that the examples may not be interpreted in any way to limit the applicability of the technology provided by the present invention to specific application in these examples.

Example 1

Growth Kinetics of a New Strain of MVA in Selected Cell Lines and Replication in Vivo (1.1) Growth Kinetics in Cell Lines To characterize a newly isolated strain of the present invention (further referred to as MVA-BN) the growth kinetics of the new strain were compared to those of known MVA strains that have already been characterized.

The experiment compared the growth kinetics of the following viruses in the subsequently listed primary cells and cell lines:

MVA-BN (Virus stock #23, 18. 02. 99 crude, titrated at $2.0 \times 10^7$ $TCID_{50}$/ml);

MVA as characterized by Altenburger (U.S. Pat. No. 5,185,146) and further referred to as MVA-HLR;

MVA (passage 575) as characterized by Anton Mayr (Mayr, A., et al. [1975] Infection 3; 6–14) and further referred to as MVA-575 (ECACC V00120707); and MVA-Vero as characterized in the International Patent Application PCT/EP01/02703 (WO 01/68820); Virus stock, passage 49, #20, 22.03.99 crude, titred at $4.2 \times 10^7$ $TCID_{50}$/ml.

| The primary cells and cell lines used were: | |
|---|---|
| CEF | Chicken embryo fibroblasts (freshly prepared from SPF eggs); |
| HeLa | Human cervix adenocarcinoma (epithelial), ATCC No. CCL-2; |
| 143B | Human bone osteosarcoma TK-, ECACC No. 91112502; |
| HaCaT | Human keratinocyte cell line, Boukamp et al 1988, J Cell Biol 106(3): 761–771; |
| BHK | Baby hamster kidney, ECACC 85011433; |
| Vero | African green monkey kidney fibroblasts, ECACC 85020299; |
| CV1 | African green monkey kidney fibroblasts, ECACC 87032605. |

For infection the cells were seeded onto 6-well-plates at a concentration of $5\times10^5$ cells/well and incubated overnight at 37° C., 5% $CO_2$ in DMEM (Gibco, Cat. No. 61965-026) with 2% FCS. The cell culture medium was removed and cells were infected at approximately moi 0.05 for one hour at 37° C., 5% $CO_2$ (for infection it is assumed that cell numbers doubled over night). The amount of virus used for each infection was $5\times10^4$ $TCID_{50}$ and is referred to as Input. The cells were then washed 3 times with DMEM and finally 1 ml DMEM, 2% FCS was added and the plates were left to incubate for 96 hours (4 days) at 37° C., 5% $CO_2$. The infections were stopped by freezing the plates at −80° C.; followed by titration analysis.

Titration Analysis (Immunostaining with a Vaccinia Virus Specific Antibody)

For titration of amount of virus test cells (CEF) were seeded on 96-well-plates in RPMI (Gibco, Cat. No. 61870-010), 7% FCS, 1% Antibiotic/Antimycotic (Gibco, Cat. No. 15240-062) at a concentration of $1\times10^4$ cells/well and incubated over night at 37° C., 5% $CO_2$. The 6-well-plates containing the infection experiments were frozen/thawed 3 times and dilutions of $10^{-1}$ to $10^{-12}$ were prepared using RPMI growth medium. Virus dilutions were distributed onto test cells and incubated for five days at 37° C., 5% $CO_2$ to allow CPE (cytopathic effect) development. Test cells were fixed (Acetone/Methanol 1:1) for 10 min, washed with PBS and incubated with polyclonal vaccinia virus specific antibody (Quartett Berlin, Cat. No. 9503-2057) at a 1:1000 dilution in incubation buffer for one hour at RT. After washing twice with PBS (Gibco, Cat. No. 20012-019) the HPR-coupled anti-rabbit antibody (Promega Mannheim, Cat. No. W4011) was added at a 1:1000 dilution in incubation buffer (PBS containing 3% FCS) for one hour at RT. Cells were again washed twice with PBS and incubated with staining solution (10 ml PBS+200 µl saturated solution of o-dianisidine in 100% ethanol+15 µl $H_2O_2$ freshly prepared) until brown spots were visible (two hours). Staining solution was removed and PBS was added to stop the staining reaction. Every well exhibiting a brown spot was marked as positive for CPE and the titer was calculated using the formula of Kaerber ($TCID_{50}$ based assay) (Kaerber, G. 1931. Arch. Exp. Pathol. Pharmakol. 162, 480).

Figure 1B:
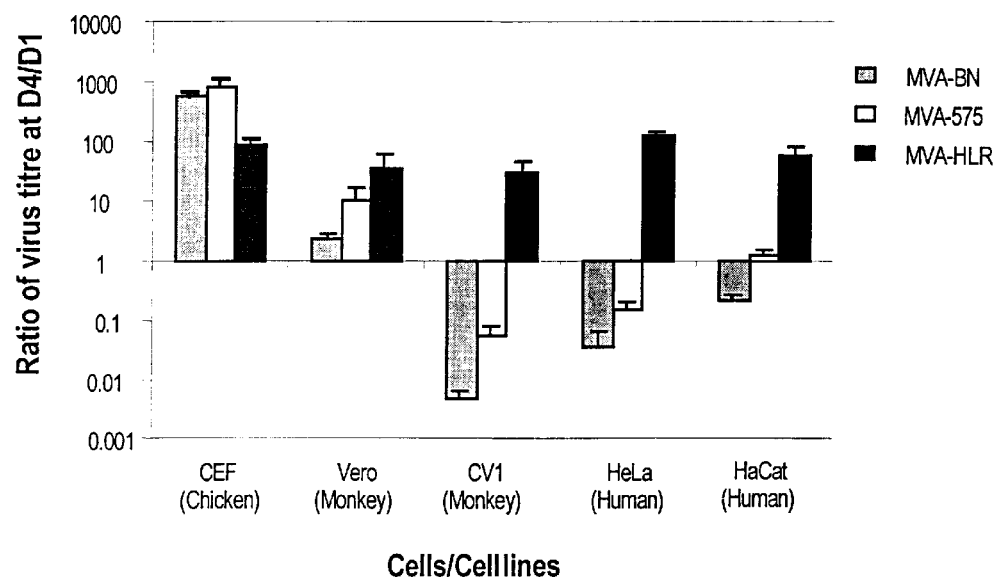

The viruses were used to infect duplicate sets of cells that were expected to be permissive for MVA (i.e., CEF and BHK) and cells expected to be non-permissive for MVA (i.e., CV-1, Vero, Hela, 143B and HaCat). The cells were infected at a low multiplicity of infection, i.e., 0.05 infectious units per cell ($5\times10^4$ $TCID_{50}$). The virus inoculum was removed and the cells were washed three times to remove any remaining unabsorbed viruses. Infections were left for a total of 4 days when viral extracts were prepared and then titred on CEF cells. Table 1 and FIG. 1 show the results of the titration assays where values are given as total amount of virus produced after 4 days infection.

It was demonstrated that all viruses amplified well in CEF cells as expected, since this is a permissive cell line for all MVAs. Additionally, it was demonstrated that all viruses amplified well in BHK (Hamster kidney cell line). MVA-Vero performed the best, since BHK is a permissive cell line for this strain.

Concerning replication in Vero cells (Monkey kidney cell line), MVA-Vero amplified well, as expected, i.e., 1000 fold above Input. MVA-HLR and also MVA-575 amplified well with a 33-fold and 10-fold increase above Input, respectively. Only MVA-BN was found to not amplify as well in these cells when compared to the other strains, i.e., only a 2-fold increase above Input.

Also concerning replication in CV1 cells (Monkey kidney cell line), it was found that MVA-BN is highly attenuated in this cell line. It exhibited a 200-fold decrease below Input. MVA-575 did not amplify above the Input level and also exhibited a slight negative amplification, i.e., 16-fold decrease below Input. MVA-HLR amplified the best with a 30-fold increase above Input, followed by MVA-Vero with 5-fold increase above Input.

It is most interesting to compare the growth kinetics of the various viruses in human cell lines. Regarding reproductive replication in 143B cells (human bone cancer cell line) it was demonstrated that MVA-Vero was the only strain to show amplification above Input (3-fold increase). All other viruses did not amplify above Input, however there was a big difference between the MVA-HLR and both MVA-BN and MVA-575. MVA-HLR was "borderline" (1-fold decrease below Input), whereas MVA-BN exhibited the greatest attenuation (300-fold decrease below Input), followed by MVA-575 (59-fold decrease below Input). To summarize, MVA-BN is superior with respect to attenuation in human 143B cells.

Furthermore, concerning replication in HeLa cells (human cervix cancer cells) it was demonstrated that MVA-HLR amplified well in this cell line, and even better than it did in the permissive BHK cells (Hela=125-fold increase above Input; BHK=88-fold increase above Input) MVA-Vero also amplified in this cell line (27-fold increase above Input). However, MVA-BN, and also to a lesser extent MVA-575, were attenuated in these cell lines (MVA-BN=29-fold decrease below Input and MVA-575=6-fold decrease below Input).

Concerning the replication in HaCat cells (human keratinocyte cell line), it was demonstrated that MVA-HLR amplified well in this cell line (55-fold increase above Input). Both MVA-Vero adapted and MVA-575 exhibited amplification in this cell line (1.2 and 1.1-fold increase above Input, respectively). However, MVA-BN was the only one to demonstrate attenuation (5-fold decrease below Input).

From this experimental analysis, we may conclude that MVA-BN is the most attenuated strain in this group of viruses. MVA-BN demonstrates extreme attenuation in human cell lines by exhibiting an amplification ratio of 0.05 to 0.2 in human embryo kidney cells (293: ECACC No. 85120602)(data not incorporated in Table 1). Furthermore, it exhibits an amplification ratio of about 0.0 in 143B cells; an amplification ratio of about 0.04 in HeLa cells; and an amplification ratio of about 0.22 in HaCat cells. Additionally, MVA-BN exhibits an amplification ratio of about 0.0 in CV1 cells. Amplification in Vero cells can be observed (ratio of 2.33), however, not to the same extent as in permissive cell lines such as BHK and CEF (compare to Table 1). Thus, MVA-BN is the only MVA strain exhibiting an amplification ratio of less than 1 in each human cell line examined, i.e., 143B, Hela, HaCat, and 293.

MVA-575 exhibits a profile similar to that of MVA-BN, however it is not as attenuated as MVA-BN.

MVA-HLR amplified well in all (human or otherwise) cell lines tested, except for 143B cells. Thus, it can be regarded as replication competent in all cell lines tested, with the exception of 143B cells. In one case, it even amplified better in a human cell line (HeLa) than in a permissive cell line (BHK).

MVA-Vero does exhibit amplification in all cell lines, but to a lesser extent than demonstrated by MVA-HLR (ignoring the 143B result). Nevertheless, it cannot be considered as being in the same "class" with regards to attenuation, as MVA-BN or MVA-575.

1.2 Replication in Vivo

Given that some MVA strains clearly replicate in vitro, different MVA strains were examined with regard to their ability to replicate in vivo using a transgenic mouse model AGR129. This mouse strain has targeted gene disruptions in the IFN receptor type I (IFN-α/β) and type II (IFN-γ) genes, and in RAG. Due to these disruptions, the mice have no IFN system and are incapable of producing mature B and T cells and, as such, are severely immune-compromised and highly susceptible to a replicating virus. Groups of six mice were immunized (i.p) with $10^7$ pfu of either MVA-BN, MVA-HLR or MVA 572 (used in 120,000 people in Germany) and monitored daily for clinical signs. All mice vaccinated with MVA HLR or MVA 572 died within 28 and 60 days, respectively. At necropsy, there were general signs of severe viral infection in the majority of organs. A standard plaque assay measured the recovery of MVA ($10^8$ pfu) from the ovaries. In contrast, mice vaccinated with the same dose of MVA-BN (corresponding to the deposited strain ECACC V00083008) survived for more than 90 days and no MVA could be recovered from organs or tissues.

When taken together, data from the in vitro and in vivo studies clearly demonstrate that MVA-BN is more highly attenuated than the parental and commercial MVA-HLR strain, and may be safe for administration to immune-compromised subjects.

Example 2

Immunological and in Vivo Data in Animal Model Systems

These experiments were designed to compare different dose and vaccination regimens of MVA-BN compared to other MVAs in animal model systems.

2.1. Different Strains of MVA Differ in their Ability to Stimulate the Immune Response.

Replication competent strains of vaccinia induce potent immune responses in mice and at high doses are lethal. Although MVA are highly attenuated and have a reduced ability to replicate on mammalian cells, there are differences in the attenuation between different strains of MVA. Indeed, MVA BN appears to be more attenuated than other MVA strains, even the parental strain MVA 575. To determine whether this difference in attenuation affects the efficacy of MVA to induce protective immune responses, different doses of MVA BN and MVA 575 were compared in a lethal vaccinia challenge model. The levels of protection were measured by a reduction in ovarian vaccinia titres determined 4 days post challenge, as this allowed a quantitative assessment of different doses and strains of MVA.

Lethal Challenge Model

Specific pathogen-free 6–8-week-old female BALB/c (H-2d mice (n=5) were immunized (i.p.) with different doses ($10^2$, $10^4$ or $10^6$ TCID$_{50}$/ml) of either MVA BN or MVA 575. MVA-BN and MVA-575 had been propagated on CEF cells, and had been sucrose purified and formulated in Tris pH 7.4. Three weeks later the mice received a boost of the same dose and strain of MVA, which was followed two weeks later by a lethal challenge (i.p.) with a replication competent strain of vaccinia. As replication competent vaccinia virus (abbreviated as "rVV") either the strain WR-L929 TK+ or the strain IHD-J were used. Control mice received a placebo vaccine. The protection was measured by the reduction in ovarian titres determined 4 days post challenge by standard plaque assay. For this, the mice were sacrificed on day 4 post the challenge and the ovaries were removed, homogenized in PBS (1 ml) and viral titres determined by standard plaque assay using VERO cells (Thomson, et al., 1998, J. Immunol. 160: 1717).

Figure 2:
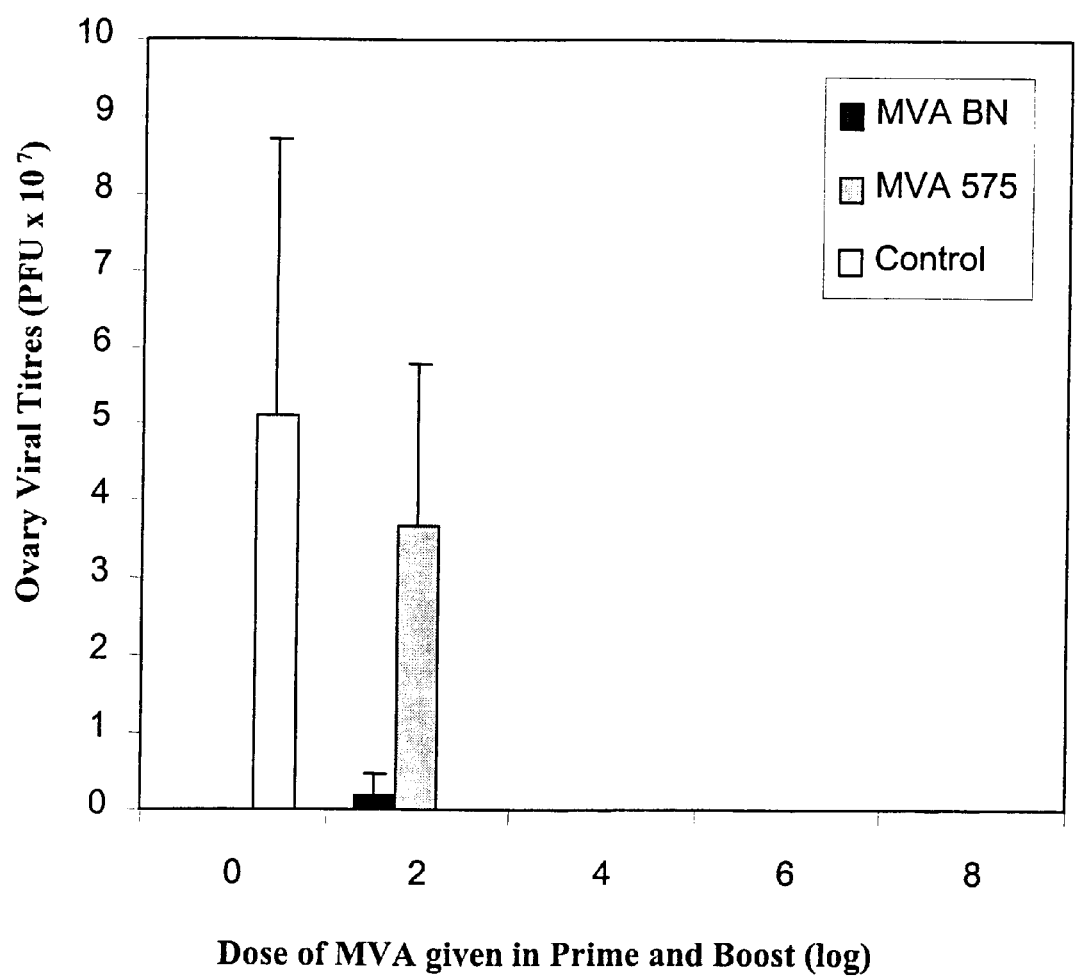
FIG. 2: Protection provided against a lethal challenge of vaccinia following vaccinations with either MVA-BN or MVA 575. The protection is measured by the reduction in ovarian titres determined 4 days post challenge by standard plaque assay.

Mice vaccinated with two immunizations of either $10^4$ or $10^6$ TCID$_{50}$/ml of MVA-BN or MVA-575 were completely protected as judged by a 100% reduction in ovarian rVV titres 4 days post challenge (FIG. 2). The challenge virus was cleared. However, differences in the levels of protection afforded by MVA-BN or MVA-575 were observed at lower doses. Mice that received two immunizations of $10^2$ TCID$_{50}$/ml of MVA 575 failed to be protected, as judged by high ovarian rVV titres (mean $3.7 \times 10^7$ pfu +/− $2.11 \times 10^7$). In contrast, mice vaccinated with the same dose of MVA-BN exhibited a significant reduction (96%) in ovarian rVV titres (mean $0.21 \times 10^7$ pfu +/− $0.287 \times 10^7$). The control mice that received a placebo vaccine had a mean viral titre of $5.11 \times 10^7$ pfu (+/− $3.59 \times 10^7$) (FIG. 2).

Both strains of MVA induce protective immune responses in mice against a lethal rVV challenge. Although both strains of MVA are equally efficient at higher doses, differences in their efficacy are clearly evident at sub-optimal doses. MVA-BN is more potent than its parent strain MVA-575 at inducing a protective immune response against a lethal rVV challenge, which may be related to the increased attenuation of MVA-BN compared to MVA-575.

2.2. MVA-BN in Prime/Boost Vaccination Regimes 2.2.1.: Induction of Antibodies to MVA Following Vaccination of Mice with Different Smallpox Vaccines The efficacy of MVA-BN was compared to other MVA and vaccinia strains previously used in the eradication of smallpox. These included single immunizations using the Elstree and Wyeth vaccinia strains produced in CEF cells and given via tail scarification, and immunizations using MVA 572 that was previously used in the smallpox eradication program in Germany. In addition, both MVA-BN and MVA 572 were compared as a pre-vaccine followed by Elstree via scarification. For each group eight BALB/c mice were used and all MVA vaccinations ($1 \times 10^7$ TCID$_{50}$) were given subcutaneous at week 0 and week 3. Two weeks following the boost immunization the mice were challenged with vaccinia (IHD-J) and the titres in the ovaries were determined 4 days post challenge. All vaccines and regimes induced 100% protection.

Figure 11:
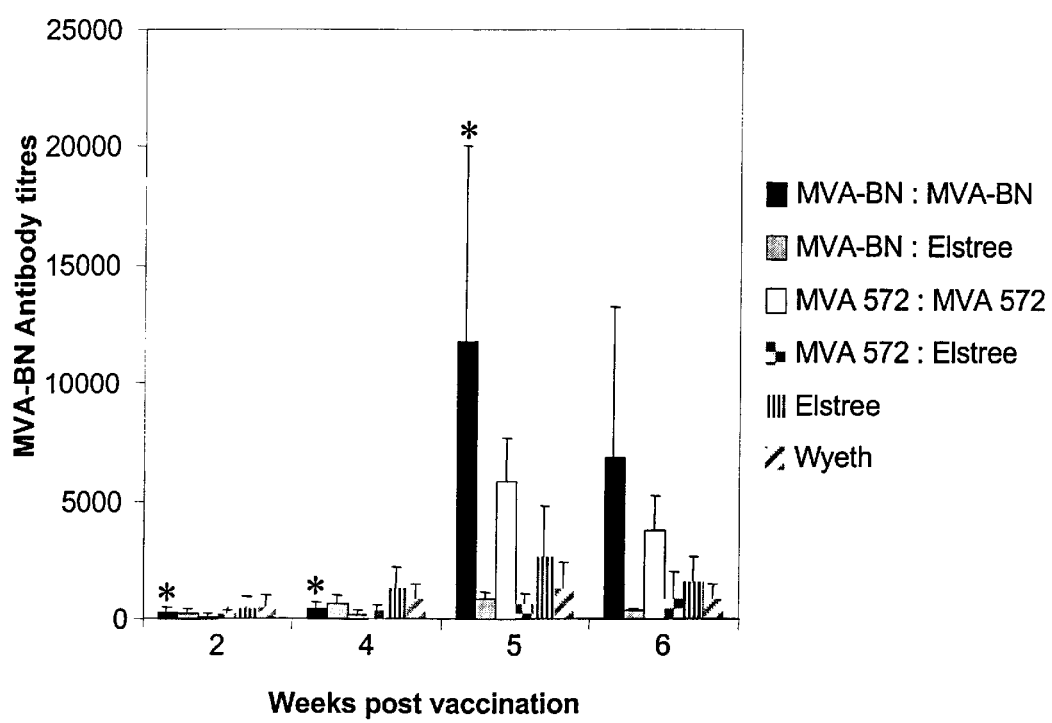
FIG. 11: Induction of antibodies to MVA following vaccination of mice with different smallpox vaccines. The levels of antibodies generated to MVA following vaccination with MVA-BN (week 0 and 4), was compared to conventional vaccinia strains, Elstree and Wyeth, given via tail scarification (week 0), MVA 572 (week 0 and 4), and MVA-BN and MVA 572 given as a pre-Elstree vaccine. MVA 572 has been deposited at the European Collection of Animal Cell Cultures as ECACC V94012707. The titres were determined using a capture ELISA and calculated by linear regression using the linear part of the graph and defined as the dilution that resulted in an optical density of 0.3. * MVA-BN: MVA-BN is significantly (p>0.05) different to MVA 572: MVA 572.

The immune responses induced using these different vaccines or regimes were measured in animals prior to challenge. Assays to measure levels of neutralizing antibodies, T cell proliferation, cytokine production (IFN-γ vs IL-4) and IFN-γ production by T cells were used. The level of the T cell responses induced by MVA-BN, as measured by ELIspot, was generally equivalent to other MVA and vaccinia viruses demonstrating bio-equivalence. A weekly analysis of the antibody titres to MVA following the different vaccination regimes revealed that vaccinations with MVA-BN significantly enhanced the speed and magnitude of the antibody response compared to the other vaccination regimes (FIG. 11). Indeed, the antibody titres to MVA were significantly higher (p>0.05) at weeks 2, 4 and 5 (1 week post boost at week 4) when vaccinated with MVA-BN compared to mice vaccinated with MVA 572. Following the boost vaccination at week 4, the antibody titres were also significantly higher in the MVA-BN group compared to the mice receiving a single vaccination of either the vaccinia strains Elstree or Wyeth. These results clearly demonstrate that 2 vaccinations with MVA-BN induced a superior antibody response compared to the classical single vaccination with traditional vaccinia strains (Elstree and Wyeth) and confirm the findings from section 1.5 that MVA-BN induces a higher specific immunity than other MVA strains.

2.2.2.: MVA-prime and Boost Regimes Generate the Same Level of Protection as DNA-prime/MVA-boost Regimes in an Influenza Challenge Model The efficacy of MVA prime/boost regimes to generate high avidity CTL responses was assessed and compared to DNA prime/MVA boost regimes that have been reported to be superior. The different regimes were assessed using a murine polytope construct encoded by either a DNA vector or MVA-BN and the levels of CTL induction were compared by ELISPOT; whereas the avidity of the response was measured as the degree of protection afforded following a challenge with influenza.

Constructs

The DNA plasmid encoding the murine polytope (10 CTL epitopes including influenza, ovalbumin) was described previously (Thomson, et al., 1998, J. Immunol. 160: 1717). This murine polytope was inserted into deletion site II of MVA-BN, propagated on CEF cells, sucrose purified and formulated in Tris pH 7.4.

Vaccination Protocols

In the current study, specific pathogen free 6–8 week old female BALB/c (H-2d) mice were used. Groups of 5 mice were used for ELISPOT analysis, whereas 6 mice per group were used for the influenza challenge experiments. Mice were vaccinated with different prime/boost regimes using MVA or DNA encoding the murine polytope, as detailed in the results. For immunizations with DNA, mice were given a single injection of 50 $\mu$g of endotoxin-free plasmid DNA (in 50 $\mu$l of PBS) in the quadricep muscle. Primary immunizations using MVA were done either by intravenous administration of $10^7$ pfu MVA-BN per mouse, or by subcutaneous administration of $10^7$ pfu or $10^8$ pfu MVA-BN per mouse. Boost immunizations were given three weeks post primary immunization. Boosting with plasmid DNA was done in the same way as the primary immunization with DNA (see above). In order to establish CTL responses, standard ELISPOT assays (Schneider et al., 1998, Nat. Med. 4; 397–402) were performed on splenocytes 2 weeks after the last booster immunization using the influenza CTL epitope peptide, the P. Berghei epitope peptide, the Cytomegalovirus peptide epitope and/or the LCV peptide epitope.

For the challenge experiments, mice were infected i.n. with a sub-lethal dose of influenza virus, Mem71 ($4.5\times10^5$ pfu in 50 ml PBS). At day 5 post-infection, the lungs were removed and viral titres were determined in duplicate on Madin-Darby canine kidney cell line using a standard influenza plaque assay.

Results

Figure 3:
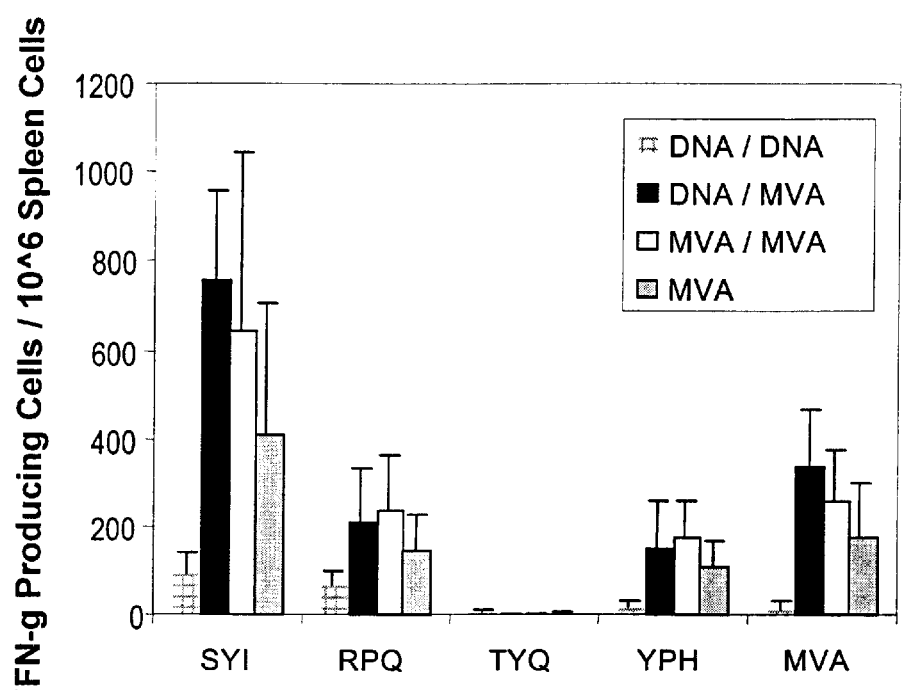
FIG. 3: Induction of CTL and protection provided against an influenza challenge using different prime/boost regimes. 3A: Induction of CTL responses to 4 different H-2d restricted epitopes following vaccination with different combinations of DNA or MVA-BN vaccines encoding a murine polytope. BALB/c mice (5 per group) were vaccinated with either DNA (intramuscular) or MVA-BN (subcutaneous) and received booster immunizations three weeks later. CTL responses to 4 different epitopes encoded by the vaccines (TYQRTRALV, infuenza; SYIPSAEKI, P. Berghei; YPHFMPTNL, cytomegalovirus; RPQASGVYM, LCV) were determined using an ELISPOT assay 2 weeks post booster immunizations. 3B: Induction of CTL responses to 4 different epitopes following vaccination with different combinations of DNA or MVA-BN vaccines encoding a murine polytope. BALB/c mice (5 per group) were vaccinated with either DNA (intramuscular) or MVA-BN (intraveneous) and received booster immunizations three weeks later. CTL responses to 4 different epitopes encoded by the vaccines (TYQ, influenza; SYI, P. Berghei; cytomegalovirus; RPQ, LCV) were determined using an ELISPOT assay 2 weeks post booster immunizations. 3C: Frequency of peptide and MVA specific T cells following homologous prime/boost using an optimal dose ($1 \times 10^8$ $TCID_{50}$) of recombinant MVA-BN, administered subcutaneous. Groups of 8 mice were vaccinated with two shots of the combinations as indicated in the figure. Two weeks after the final vaccination, peptide-specific splenocytes were enumerated using an IFN-gamma ELISPOT assay. The bars represent the mean number of specific spots plus/minus the standard deviation from the mean.
Figure 3:
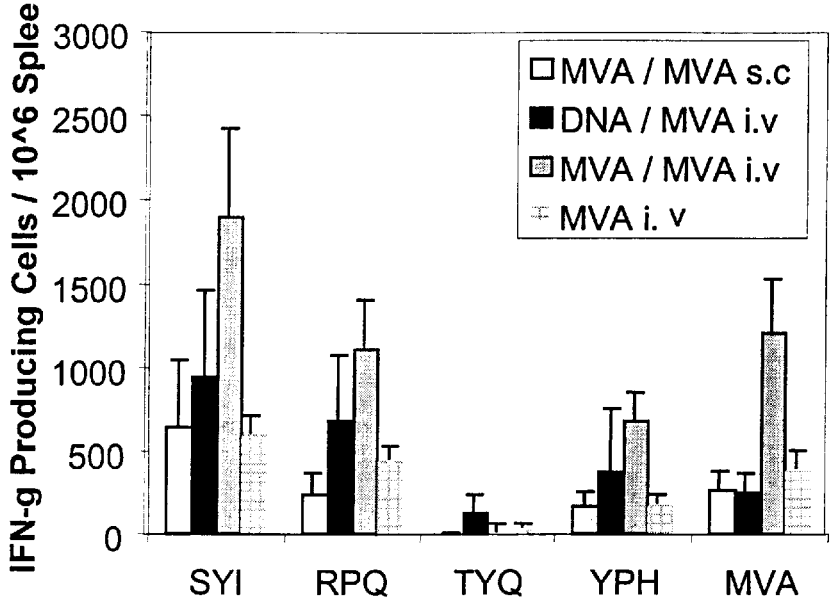

Using the DNA vaccine alone, the induction of CTL to the 4 H-2d epitopes encoded by the murine polytope was poor and only weak responses could be detected to two of the epitopes for P. Berghei and lymphocytic choriomeningitis virus. In contrast, using a DNA prime/MVA boost regime ($10^7$ pfu MVA-BN given subcutaneous) there were significantly more CTL induced to SLY (8-fold increase) and RPQ (3-fold increase) and responses were also observed to a third epitope for murine cytomegalovirus (FIG. 3A). However, $10^7$ pfu MVA-BN given subcutaneous in a homologous prime/boost regime induced the same level of response as DNA followed by MVA-BN (FIG. 3A). Surprisingly, there was no significant difference in the numbers of CTLs induced to the three epitopes when one immunization of MVA-BN ($10^7$ TCID$_{50}$) was used, indicating that a secondary immunization with MVA-BN did not significantly boost CTL responses.

Figure 3C:
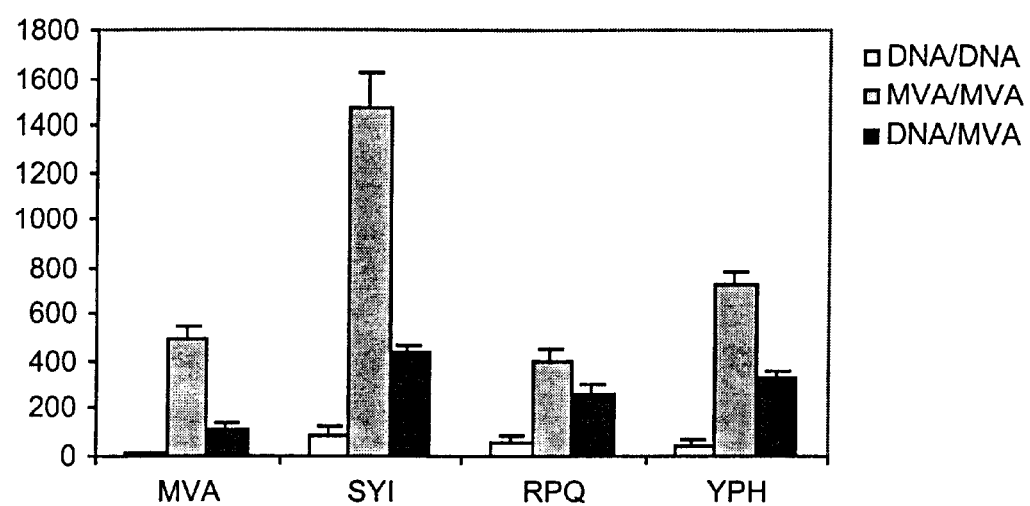

The subcutaneous administration of $10^7$ pfu MVA has previously been shown to be the most inefficient route and virus concentration for vaccination using other strains of MVA; particularly when compared to intravenous immunizations (Schneider, et al. 1998). In order to define optimal immunization regimes, the above protocol was repeated using various amounts of virus and modes of administration. In one experiment, $10^7$ pfu MVA-BN was given intravenously (FIG. 3B). In another experiment, $10^8$ pfu MVA-BN was administered subcutaneous (FIG. 3C). In both of these experiments, MVA-BN prime/boost immunizations induced higher mean CTL numbers to all three CTL epitopes when compared to DNA prime/MVA boost regimes. Also unlike $10^7$ pfu MVA-BN administered subcutaneous, immunization with $10^7$ pfu MVA-BN given intravenously and immunization with $10^8$ pfu given subcutaneous significantly boosted the CTL response. This clearly indicates that MVA-BN can be used to boost CTL responses in the presence of a pre-existing immunity to the vector.

2.2.3.: Efficacy of a MVA-BN Nef Vaccine in SIV Infected Rhesus Monkeys

To determine the efficacy of a MVA-BN nef vaccine, the viral load and delay of disease following a challenge with a virulent primary isolate of SIV were assessed. Another objective of the study was to determine whether MVA-BN could be used to safely boost immune responses in immune-compromised monkeys with a pre-existing immunity to MVA.

Vaccination Protocols

Two groups (n=6) of rhesus monkeys (*Macaca mulatto*) were vaccinated with a bolus intramuscular injection using either MVA-BN alone or a recombinant MVA-BN nef at week 0, 8 and 16. On week 22, all monkeys were challenged with 50 MID$_{50}$ of a pathogenic cell-associated SIV stock (1×C) from primary, uncultured rhesus monkey PBMC by the intravenous route. The clinical status of the animals was frequently monitored and regular blood samples were taken for the measurement of viremia, immune parameters, and a full range of hematology and blood clinical chemistry parameters. Animals that developed AIDs-like disease were sacrificed. The surviving monkeys were monitored for 99 weeks post vaccination. At week 100 the surviving monkeys were immunized i.m. with MVA-BN tat and received further immunizations with the same MVA-BN tat at week 102 and 106.

Figure 4:
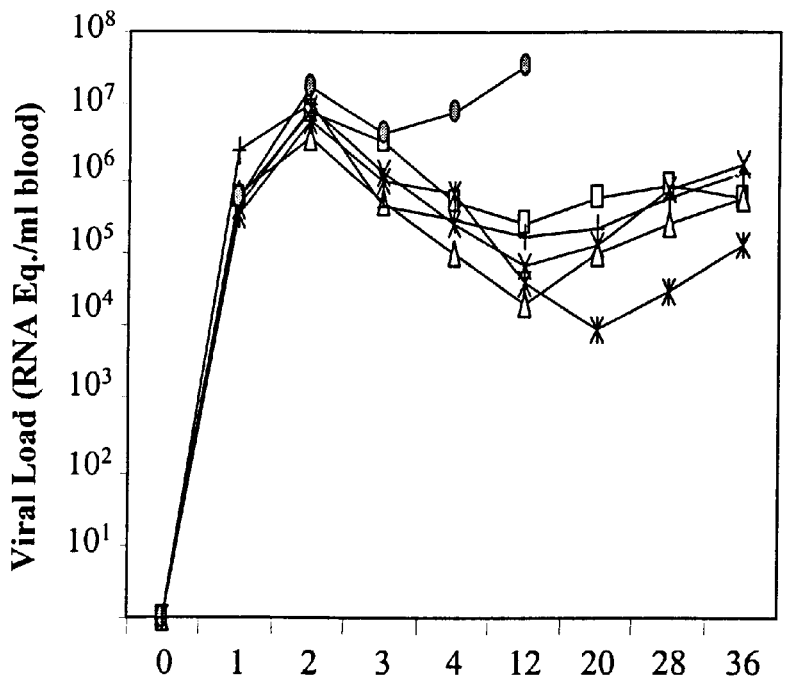
FIG. 4: SIV load of monkeys vaccinated with MVA-BN nef or MVA-BN.
Figure 5:
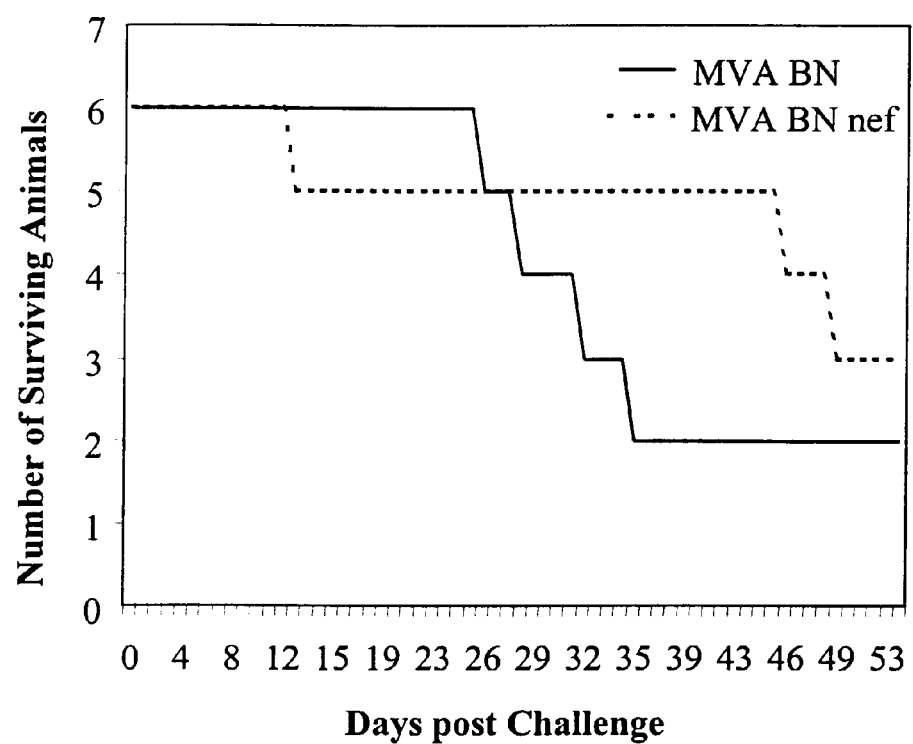
FIG. 5: Survival of vaccinated monkeys following infection with SIV.
Figure 6:
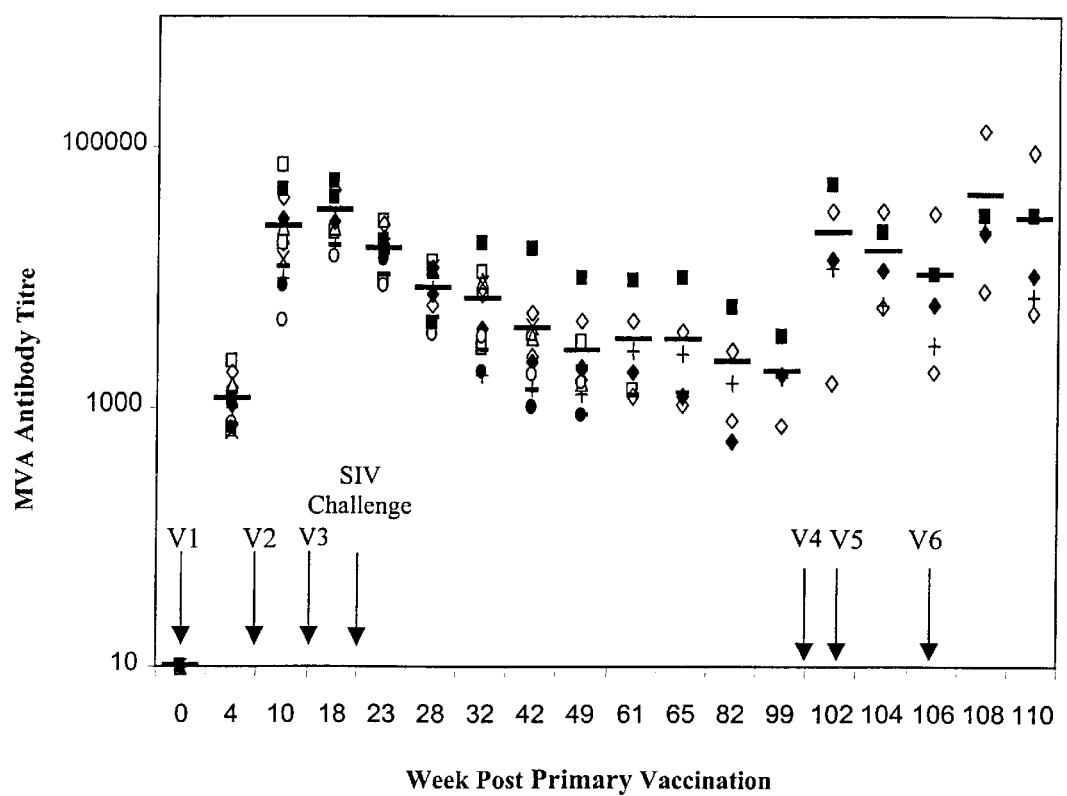
FIG. 6: Monkey serum antibody titres to MVA-BN. The antibody titres for each animal are shown as different shapes, whereas the mean titre is illustrated as a solid rectangle.

No adverse effects were observed following any of the vaccinations with either MVA-BN or MVA-BN nef. Following the infection of the monkeys with SIV, the levels of viremia rose sharply and peaked two weeks post infection (FIG. 4). Due to the large standard deviations within the groups, there was no significant difference in the mean levels of SIV between the groups vaccinated with MVA-BN nef or MVA-BN. However, there was a general 10 fold lower SIV load in the group vaccinated with the MVA-BN nef compared to the control (MVA-BN) group. Furthermore, after 35 weeks following infection (the initial observation period), only 1 out of the six monkeys vaccinated with MVA-BN nef had to be euthanised due to the severity of the disease, compared to 4 out of the 6 animals in the control group (FIG. 5). The development of disease clearly correlated with a higher virus load and, as such, the animals were observed for an additional 29 weeks post infection. The MVA-BN nef vaccine appeared to delay the progression of the disease compared to the control group, and even at week 46 post-infection 5 out of the 6 MVA-BN nef animals survived (FIG. 5). However, by week 59 post-infection, two additional animals in the nef vaccinated group were euthanised leaving five surviving animals (three from the MVA-BN nef group and two vaccinated with MVA-BN). An examination of the antibody titres generated to MVA-BN in these 12 monkeys clearly demonstrated that MVA-BN could boost the immune response even in the presence of a pre-existing immunity to MVA (FIG. 6). Following the primary immunization with either MVA-BN or MVA-BN nef, all monkeys generated an antibody response to MVA with a mean titre of 1000. This antibody response was significantly boosted following the secondary immunization, clearly demonstrating that MVA can be used to prime/boost immune response in healthy monkeys. These antibody titres gradually declined, although by week 49 post-immunization the titres plateaued, such that the mean titres to MVA at week 99 were 2000.

Figure 7:
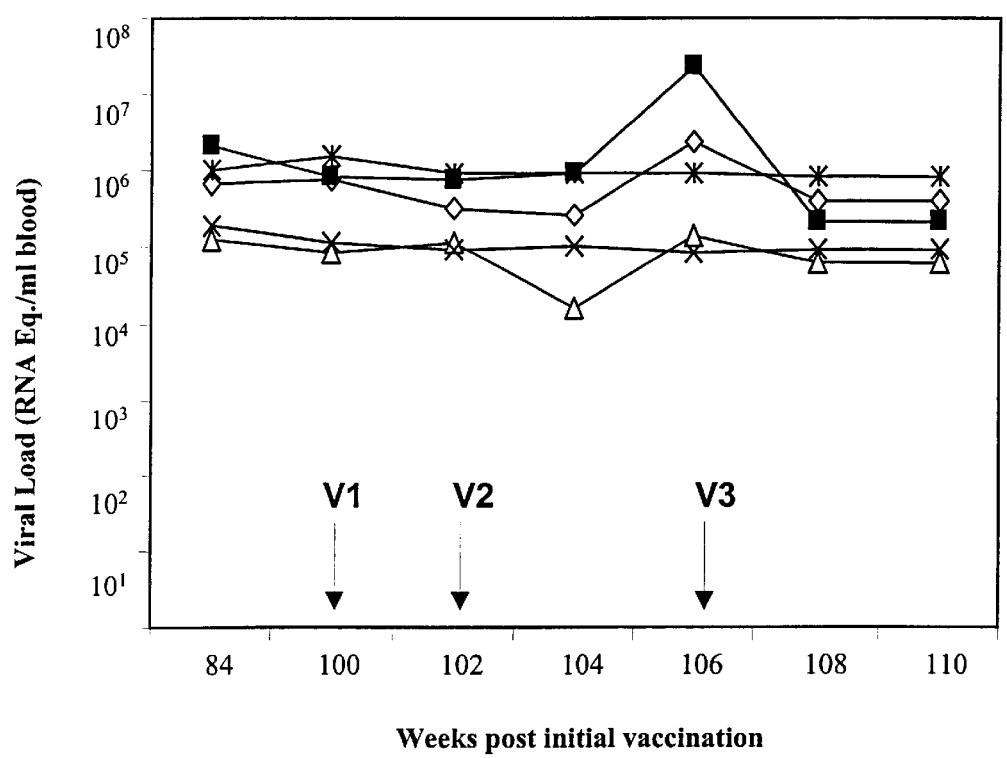
FIG. 7: Levels of SIV in immune-compromised monkeys (CD4<400 ml blood) following vaccinations with MVA-BN encoding tat. Monkeys had previously received three vaccinations with either MVA-BN or MVA-BN nef (week 0, 8, 16) and had been infected with a pathogenic isolate of SIV (week 22). At week 100, 102 and 106 (indicated by arrows) the monkeys were vaccinated with MVA-BN tat.

The five surviving monkeys were SIV infected and immune-compromised with CD4 counts lower than 400/µl blood. To investigate the impact of using MVA-BN in immune-compromised monkeys the five animals were vaccination three times with MVA-BN tat at week 100, 102 and 106 post initial vaccination. The first immunization with MVA-BN tat significantly boosted the antibody response to MVA in the immune-compromised monkeys. The response was further boosted with the third immunization six weeks later (FIG. 6). These results demonstrate that MVA-BN can boost the immune response in the presence of a significant pre-existing immunity to MVA, even in immune-compromised monkeys. Although the monkeys' immune responses were boosted following immunization with MVA-BN tat, the levels of SIV remained stable. This indicates that immunization with MVA-BN is safe and does not affect SIV levels in immune-compromised monkeys (FIG. 7).

This study demonstrated that MVA-BN is able to prime/boost immune responses in immune-compromised rhesus monkeys. It also demonstrated that MVA-BN immunizations are safe and do not affect the levels of viremia in SIV infected animals. The delay in the progression of AIDS-like disease in the animals vaccinated with the MVA-BN nef vaccine indicates that an immune response was successfully generated to nef.

2.2.4.: Therapeutic Vaccination of SIV-infected Monkeys Undergoing Anti-retroviral Treatment An MVA-BN based therapeutic HIV vaccine is likely to be used in individuals undergoing anti-retroviral therapy. Therefore, this study was designed to investigate the safety (effect on SIV levels) and efficacy of recombinant MVAs encoding a variety of SIV antigens (gag, pol, env, rev, tat, and nef) in SIV infected monkeys treated with PMPA. PMPA is a nucleoside analogue that is effective against HIV and SIV (Rosenwirth, B. et al., 2000, J Virol 74, 1704–11).

Constructs

All the recombinant MVA constructs were propagated on CEF cells, sucrose purified and formulated in Tris pH 7.4.

Vaccination Protocol

Three groups (n=6) of rhesus monkeys (*Macaca mulatta*) were infected with 50 $MID_{50}$ of a pathogenic primary SIV isolated (1×C) and then treated daily with PMPA (60 mg/kg given s.c.) for 19 weeks. At week 10, animals were vaccinated with recombinant MVA-BN (i.m.), or saline, and received identical vaccinations 6 weeks later. Group 1 received a mixture of MVA gag-pol and MVA-env, group 2 received MVA-tat, MVA-rev and MVA-nef, whereas Group 3 received saline. The clinical status of the animals was frequently monitored and regular blood samples were taken for the measurement of viremia, immune parameters, and a full range of hematology and blood clinical chemistry parameters.

Figure 8:
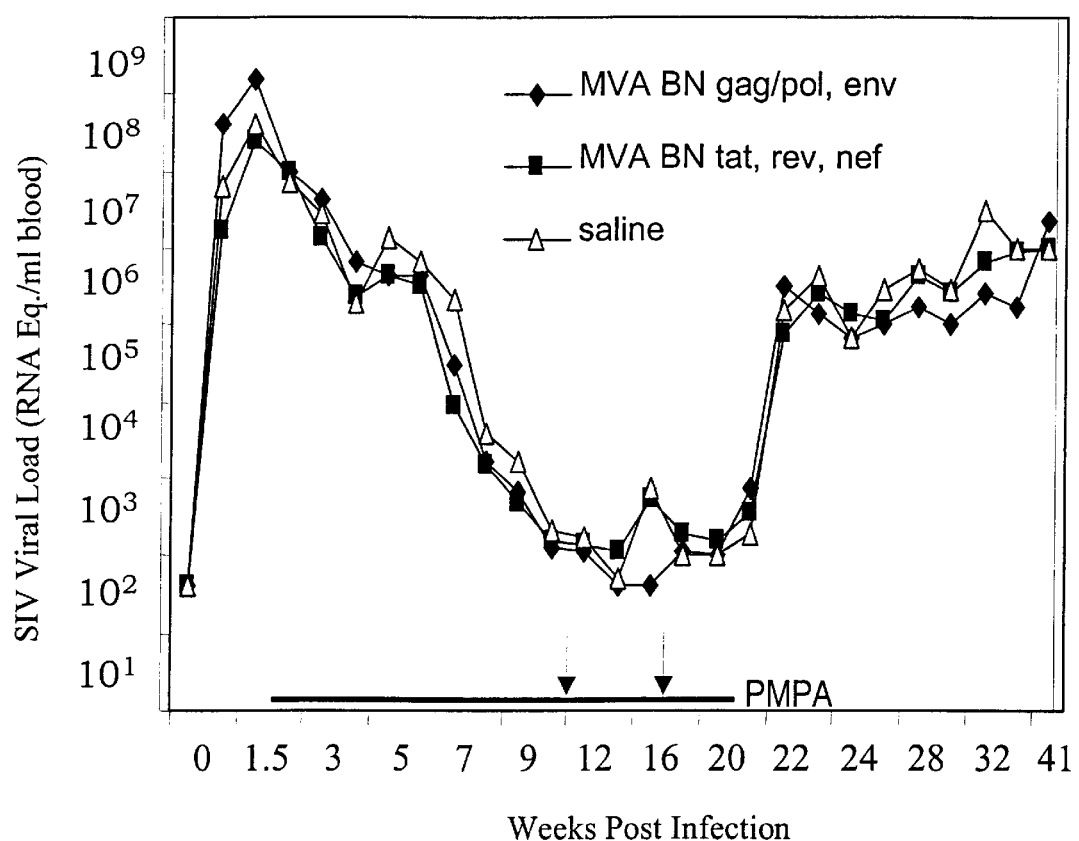
FIG. 8: SIV levels in monkeys undergoing anti-retroviral therapy and therapeutic vaccination using MVA-BN. Three groups of monkeys (n=6) were infected with SIV and treated daily with PMPA (indicated by black line). At week 10 and 16 the animals were vaccinated (indicated by arrows) with either mixtures of recombinant MVA or saline.
Figure 9:
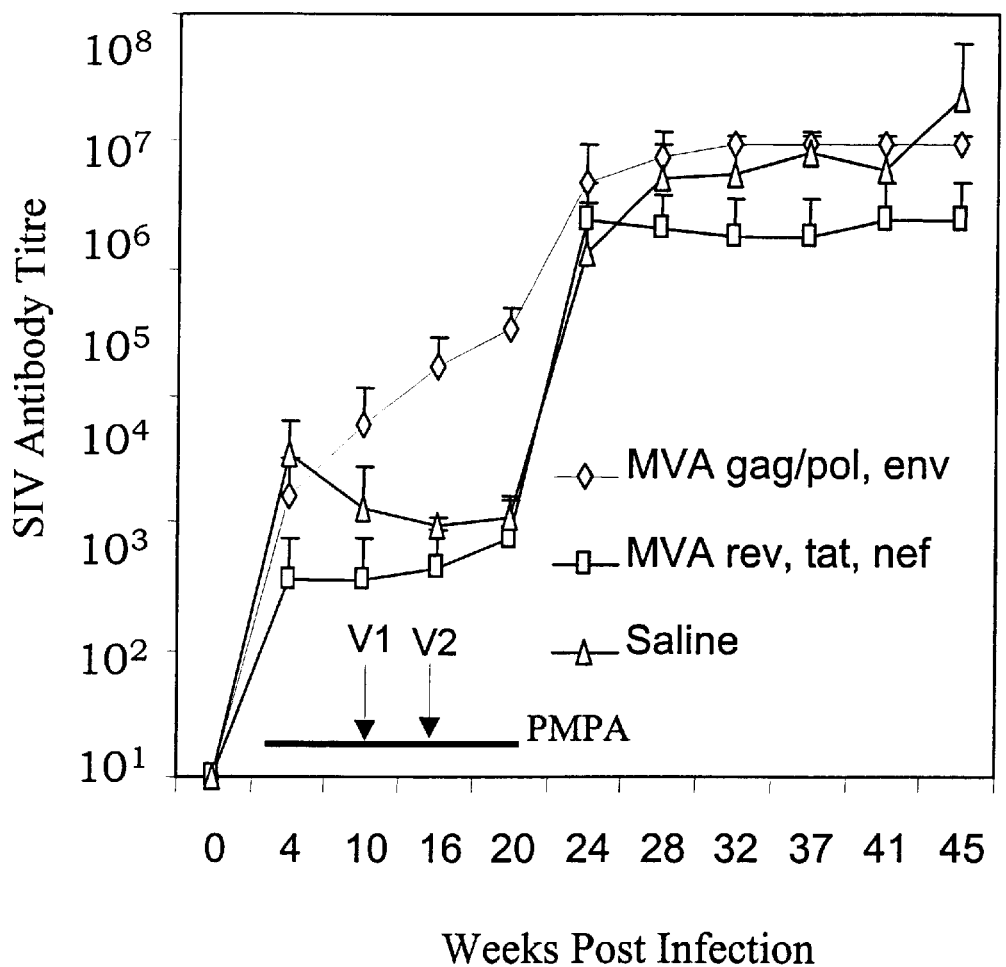
FIG. 9: Humoral response generated to SIV following infection and vaccination with recombinant MVA. Three groups (n=6) of monkeys were infected with a pathogenic isolate of SIV (week 0) and then treated with the anti-retroviral therapy (PMPA; indicated by bold line). Monkeys were vaccinated with mixtures of recombinant MVA or saline at week 10 and 16. Antibodies to SIV were determined using infected T cell lysates as antigen in a standard ELISA.
Figure 10:
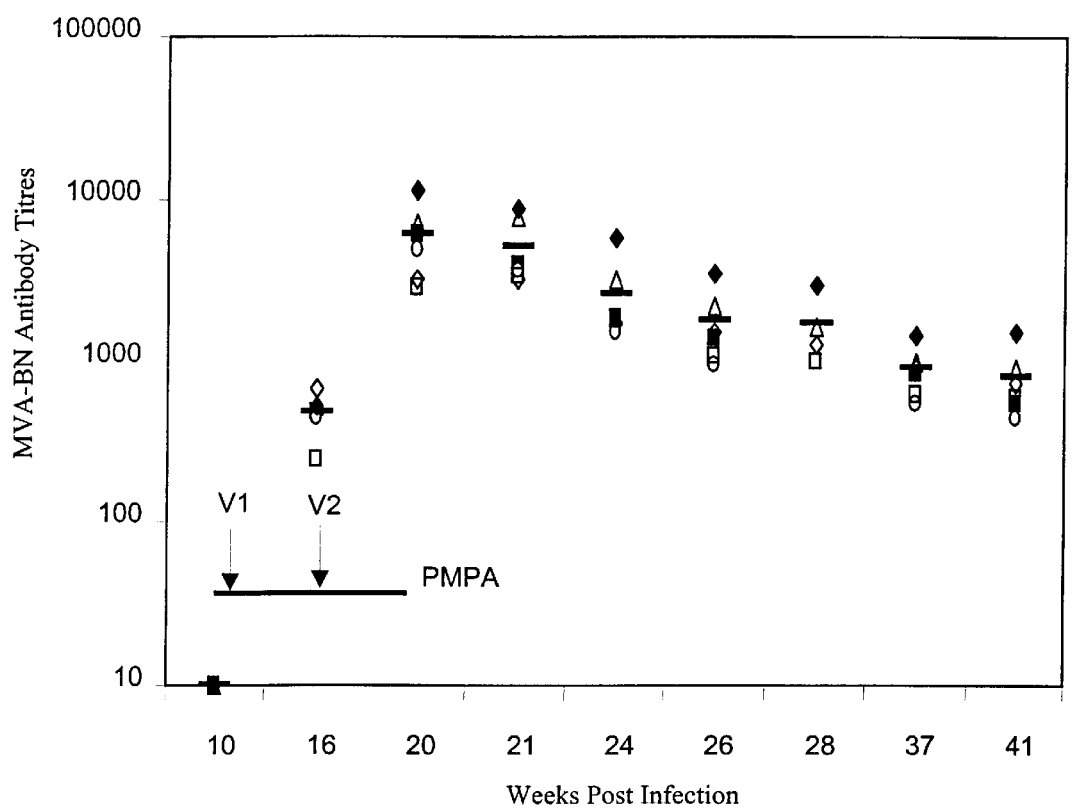
FIG. 10: Humoral response generated to MVA in SIV infected monkeys undergoing anti-retroviral therapy. Three groups (n=6) of monkeys were infected with a pathogenic isolate of SIV (week 0) and then treated with the anti-retroviral therapy (PMPA; indicated by bold line). Monkeys were vaccinated with mixtures of recombinant MVA or saline at week 10 and 16. Antibodies to MVA were determined using a standard capture ELISA for MVA.

All animals established high SIV loads that peaked 2 weeks post infection (FIG. 8). Following daily treatment with PMPA, the SIV levels decreased and stabilized to low levels by week 9. As in the previous study, vaccinations with MVA at week 10 and 16 had no effect on the SIV levels, indicating that MVA-BN is a safe vaccine vector for immune-compromised animals. Once the animals came off PMPA treatment (week 21) the SIV levels increased. Although three animals in Group 1 had reduced levels of SIV when compared to control Group 3, there was no significant difference in the mean SIV load between any of the groups following the end of PMPA treatment (FIG. 8). Using an ELISA to SIV infected T-cell lysates, animals in all groups generated an antibody response to SIV by week 4 following infection (FIG. 9). The SIV antibody titre in the control group (saline) dropped during the PMPA treatment and increased rapidly when PMPA treatment stopped, reflecting the drop and subsequent increase in SIV levels during anti-retroviral therapy (FIG. 9). A similar pattern in SIV antibody titre was observed in Group 2, which received MVA-tat, MVA-rev and MVA-nef; possibly reflecting the under-expression of these regulatory proteins in the SIV infected T cell lysates used in the ELISA. In contrast however, the anti-SIV antibody titres in Group 1 increased following the vaccinations with MVA gag-pol and MVA-env at week 10, indicating that recombinant MVA-BN can boost the immune response to SIV in (SIV) infected animals undergoing anti-retroviral therapy. Importantly, the anti-SIV antibody titres were boosted following the secondary immunization at week 16, again demonstrating that MVA can boost immune responses in immune-compromised animals, even in the presence of a pre-existing immunity to MVA (FIG. 8). The anti-MVA antibody titres in Group 1 also reflected this pattern with the generation of an antibody response following the primary immunization, and this was significantly boosted following the secondary vaccination (FIG. 10).

PHLS Public Health Laboratory Service
Centre for Applied Microbiology and Research
This document certifies that Virus Strain
(Deposit ref V94012707 ) has been accepted
as a patent deposit, in accordance with
The Budapest Treaty of 1977,
with the European Collection of Animal Cell Cultures on
27th January 1994
Dr. Alan Doyle,
Curator.

FOR THE PURPOSES 52 TENT PROCEDUR

INTERNATIONAL FORM

TO
Prof Dr Dr h.c. mult
  Anton Mayr
Bockmeyrstrasse 9
80992 Munchen
Germany
      NAME AND ADDRESS
         OF DEPOSITOR RECEIPT IN THE CASE OF AN ORIGINAL DEPOSIT
issued pursuant to Rule 7.1 by the
INTERNATIONAL DEPOSITARY AUTHORITY
identified at the bottom of this page

I. IDENTIFICATION OF THE MICROORGANISM

Identification reference given by the DEPOSITOR:
Vacciniavirus Strain MVA

Accession number given by the INTERNATIONAL DEPOSITARY AUTHORITY:
V94012707

II. SCIENTIFIC DESCRIPTION AND/OR PROPOSED TAXONOMIC DESIGNATION

The microorganism identified under I above was accompanied by:

[X] a scientific description

[ ] a proposed taxonomic designation (Mark with a cross where applicable)

III. RECEIPT AND ACCEPTANCE

This International Depositary Authority accepts the microorganism identified under I above, which was received by it on 27/1/94 (date of the original deposit)[1]

IV. RECEIPT OF REQUEST FOR CONVERSION

The microorganism identified under I above was received by this International Depositary Authority on            (date of the original deposit) and a request to convert the original deposit to a deposit under the Budapest Treaty was received by it on            (date of receipt of request for conversion)

V. INTERNATIONAL DEPOSITARY AUTHORITY

Name: Dr A. Doyle

Address: ECACC, CAMR
Porton Down
Salisbury, SP4 OJG, UK

Signature(s) of person(s) having the power to represent the International Depositary Authority or of authorized official(s):

Date: 28th June 1994

[1] Where Rule 6.4(d) applies, such date is the date on which the status of international depositary authority was acquired.

Form BP/4 (sole page)

53

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| TO<br>Prof Dr Dr h.c. mult Anton Mayr<br>Bockmeyrstrasse 9<br>80992 Munchen<br>Germany | VIABILITY STATEMENT<br>issued pursuant to Rule 10.2 by the<br>INTERNATIONAL DEPOSITARY AUTHORITY<br>identified on the following page |
|---|---|
| NAME AND ADDRESS OF THE PARTY<br>TO WHOM THE VIABILITY STATEMENT<br>IS ISSUED | |

| I. DEPOSITOR | II. IDENTIFICATION OF THE MICROORGANISM |
|---|---|
| Name: Prof Dr Dr h.c. mult Anton Mayr<br>Address: Bockmeyrstrasse 9<br>80992 Munchen<br>Germany | Accession number given by the<br>INTERNATIONAL DEPOSITARY AUTHORITY:<br>V94012707<br>Date of the deposit or of the transfer:<br>27th January 1994 |

| III. VIABILITY STATEMENT |
|---|
| The viability of the microorganism identified under II above was tested on $^1$ 27th January 1994 $^2$. On that date, the said microorganism was<br><br>$^3$ [X] viable<br><br>$^3$ [ ] no longer viable |

$^1$ Indicate the date of the original deposit or, where a new deposit or a transfer has been made, the most recent relevant date (date of the new deposit or date of the transfer).

$^2$ In the cases referred to in Rule 10.2(a)(ii) and (iii), refer to the most recent viability test.

$^3$ Mark with a cross the applicable box.

Form BP/9 (first page)

54

| IV. CONDITIONS UNDER WHICH THE VIABILITY TEST HAS BEEN PERFORMED [4] |
|---|
| |

| V. INTERNATIONAL DEPOSITARY AUTHORITY | |
|---|---|
| Name: Dr A. Doyle<br><br>Address: ECACC<br>CAMR<br>Porton Down<br>Salisbury, SP4 0JG, UK. | Signature(s) of person(s) having the power to represent the International Depositary Authority or of authorized official(s):<br><br><br><br>Date: 28th June 1994 |

[4] Fill in if the information has requested and if the results of the test were negative.

Form BP/9 (second and last page)

55

| Applicant's or agent's file reference number | BN 35 PCT | International application No. |
|---|---|---|

INDICATIONS RELATING TO A DEPOSITED MICROORGANISM (PCT Rule 13bis)

A. The indications made below relate to the microorganism referred to in the description
on page 13, line 13.

B. IDENTIFICATION OF DEPOSIT   Further deposits are identified on an additional sheet ☐

Name of depositary institution ECACC
European Collection of Cell Cultures

Address of depositary institution (including postal code and country)
Centre for Applied Microbiology & Research
Salisbury
Wiltshire SP4 OJG, United Kingdom

| Date of deposit | Accession Number |
|---|---|
| December 7, 2000 | 00120707 |

C. ADDITIONAL INDICATIONS (leave blank if not applicable)   This information is continued on an additional sheet ☐

In respect of all designated States to which such action is possible and to the extent that it is legally permissable under the law of the designated State, it is ... e of the deposited microorganism be made available only by the issue the ... expert, in accordance with the relevant patent legislation, e.g., EPC Rule 28 ( ... 1995, Schedule 2, Paragraph 3; Australian Regulation 3.25(3); Danish Pa! ... .ns 22 and 33(3) and generally similar provisions mutatis mutandis for any other designated State.

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| ☐ This sheet was received with the international application | ☐ This sheet was received by the International Bureau on: |
| Authorized officer | Authorized officer |

Form PCT/RO/...

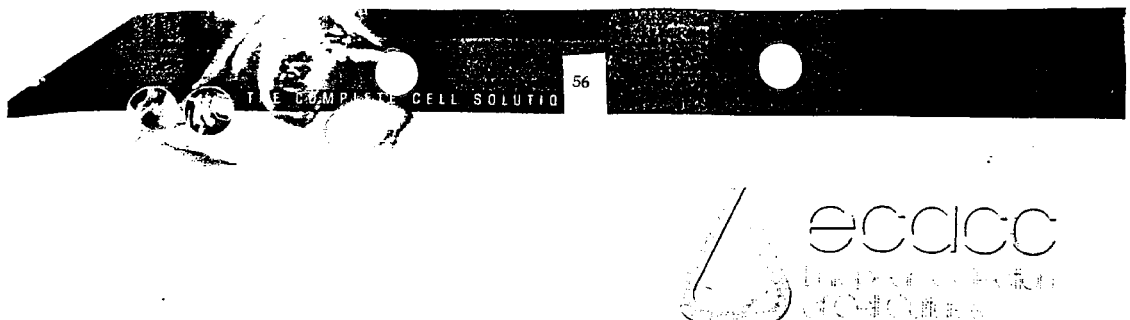

Centre for Applied Microbiology and Research
&
European Collection of Cell Cultures This document certifies that Virus
(Deposit Ref. V00120707) has been accepted as a patent deposit,
in accordance with
The Budapest Treaty of 1977,
with the European Collection of Cell Cultures on 7$^{TH}$ December 2000

...............................
Dr P J Packer
Quality Manager, ECACC

European Collection of Cell Cultures, CAMR, Salisbury, Wiltshire SP4 0JG UK.
Tel: 44 (0) 1980 612512  Fax: 44 (0) 1980 611315  Email: ecacc@camr.org.uk  Web Site: ecacc.org.uk

APPENDIX 3

Page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO

BAVARIAN NORDIC RESEARCH
INSTITUTE GMBH
FRAUNHOFERSTRASSE 18B
D-82152 MARTINSRIED
GERMANY

NAME AND ADDRESS
OF DEPOSITOR

| I. IDENTIFICATION OF THE MICROORGANISM | |
|---|---|
| Identification reference given by the DEPOSITOR:<br><br>MVA-575 | Accession number given by the INTERNATIONAL DEPOSITARY AUTHORITY:<br><br>V00120707 |

II. SCIENTIFIC DESCRIPTION AND/OR PROPOSED TAXONOMIC DESIGNATION

The microorganism identified under I above was accompanied by:

[X] A scientific description

[ ] A proposed taxonomic designation (Mark with a cross where applicable)

III. RECEIPT AND ACCEPTANCE

This International Depository Authority accepts the microorganism identified under I above, which was received by it on 7$^{TH}$ December 2000 (date of the original deposit)[1]

IV. RECEIPT OF REQUEST FOR CONVERSION

The microorganism identified under I above was received by this International
Depository Authority on                (date of the original deposit) and
A request to convert the original deposit to a deposit under the Budapest Treaty
was received by it on                (date of receipt of request for conversion)

IV. INTERNATIONAL DEPOSITORY AUTHORITY

| Name: Dr P J Packer | Signature(s) of person(s) having the power to represent the International Depository Authority or of authorized officials(s): |
|---|---|
| Address: ECACC<br>CAMR<br>Porton Down<br>Salisbury SP4 OJG | Date: |

Where Rule 6.4 applies, such date is the date on which the status of international depositary authority was acquired Form BP/4 (sole page)                1991

APPENDIX 3

Page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

```
TO

BAVARIAN NORDIC RESEARCH
INSTITUTE GMBH
FRAUNHOFERSTRASSE 18B
D-82152 MARTINSRIED
GERMANY
```

VIABILITY STATEMENT
Issued pursant to Rule 10.2 by the
INTERNATIONAL DEPOSITARY AUTHORITY
identified on the following page

```
NAME AND ADDRESS OF THE PARTY
TO WHOM THE VIABILITY OF STATEMENT
           IS ISSUED
```

| I. DEPOSITOR | II. IDENTIFICATION OF THE MICROORGANISM |
|---|---|
| Name: BAVARIAN NORDIC RESEARCH INSTITUTE GMBH<br><br>Address: FRAUNHOFERSTRASSE 18B<br>D-82152 MARTINSRIED<br>GERMANY | Accession number given by the<br>INTERNATIONAL DEPOSITORY AUTHORITY:<br><br>00120707<br><br>Date of the deposit or of the transfer:<br>7$^{TH}$ December 2000 |

II. VIABILITY STATEMENT

The viability of the microorganism identified under II above was tested
on [1]                                                  [2]. On that date, the said microorganism was ☐ [3]    viable ☐ [3]    no longer viable 1   Indicate the date of the original deposit or, where a new deposit or a transfer has been
    made, the most relevant date (date of the new deposit or date of the transfer).

2   In the cases referred to in Rule 10.2 (a) (ii) and (iii), refer to the most recent viability
    test.

3   Mark with a cross the applicable box.

Form BP/4  (first page)

Appendix 3

Page 25

| IV. CONDITIONS UNDER WHICH THE VIABILITY TEST HAS BEEN PERFORMED [4] |
|---|
| MVA-575 - V00120707<br><br>THIS VIRUS WAS TITRATED ON BHK CELLS $TCID_{50} = 10^{6.5}$ |

| V. INTERNATIONAL DEPOSITARY AUTHORITY | |
|---|---|
| Name: Dr P J Packer<br>      ECACC CAMR<br>Address: Porton Down<br>      Salisbury<br>      Wiltshire<br>      SP4 0JG | Signature(s) of person(s) having the power to represent the International Depositary Authority or of authorized official(s):<br><br>Date: 23/3/01 |

[4] Fill in if the information has been requested and if the results of the test were negative.

Form BP/9 (second and last page)

Certificate of Analysis

Product Description    MVA-575
Accession Number    00120707

---

Test Description:    Determination of $TCID_{50}$ of cytopathic Virus titration. (SOP ECACC/055) Cell Acceptance Criterion/Specification/Criteria: Negative controls should show no sign of Cytopathic effects. The Test Sample is serially diluted into in 4 wells of indicator cell lines for each dilution. Cytopathic effects indicate that virus is present. Virus titre is calculated using the below equation where x is the value obtained from a standard $TCID_{50}$ Table as a result of the distribution of the wells displaying less than 4 positive wells per dilution, and y is the value of the highest dilution where all 4 wells are positive:

$$TCID_{50} = \frac{1}{y} \times 10^{1+x}$$

Date:    19/01/01
Result:
- Indicator Cell Line:    BHK 21 CLONE 13
- Negative Control:    NO CPE
- Test Sample:    CPE
- Distribution of less that 4 positive wells:    4, 4, 0
- X:    0.50
- Y:    $10^{-5}$ $$TCID_{50} = \frac{1}{10^{-5}} \times 10^{1+0.50}$$

$$= 10^{6.5}$$

Overall Result:    Virus Present

---

Test Description:    The Detection of Mycoplasma by Isolation on Mycoplasma Pig Serum Agar and in Mycoplasma Horse Serum Broth.
SOP QC/MYCO/01/02

Acceptance Criterion/Specification:    All positive controls (*M. pneumoniae* & *M. orale*) must show evidence of mycoplasma by typical colony formation on agar plates. Broths are subcultured onto Mycoplasma Pig Serum Agar where evidence of mycoplasma by typical colony formation is evaluated. All negative control agar plates must show no evidence of microbial growth.
The criteria for a positive test result is evidence of mycoplasma by typical colony formation on agar. A negative result will show no such evidence.

Test Number:    21702
Date:    12/02/01
Result:
- Positive Control:    Positive
- Negative Control:    Negative
- Test Result:    Negative
- Overall Result:    PASS

---

Authorised by................................ECACC, Head of Quality................ Date

61

Certificate of Analysis

Product Description     MVA-575
Accession Number     00120707

Test Description:     Detection of Mycoplasma using a Vero indicator cell line and Hoechst 33258 fluorescent detection system.
SOP QC/MYCO/07/05

Acceptance Criterion/Specification: The Vero cells in the negative control are clearly seen as fluorescing nuclei with no cytoplasmic fluorescence. Positive control (*M. orale*) must show evidence of mycoplasma as fluorescing nuclei plus extra nuclear fluorescence of mycoplasma DNA. Positive test results appear as extra nuclear fluorescence of mycoplasma DNA. Negative results show no cytoplasmic fluorescence.

Test Number:     21702

Date:     12/02/01

Result:

| | |
|---|---|
| Positive Control: | Positive |
| Negative Control: | Negative |
| Test Result: | Negative |
| Overall Result: | PASS |

Test Description:     Detection of bacteria and fungi by isolation on Tryptone Soya Broth (TSB) and in Fluid Thioglycollate Medium (FTGM). SOP QC/BF/01/02

Acceptance Criterion/Specification: All positive controls (*Bacillis subtilus*, *Clostridium sporogenes* and *Candida albicans*) show evidence of microbial growth (turbidity) and the negative controls show no evidence of microbial growth (clear).
The criteria for a positive test is turbidity in any of the test broths. All broths should be clear for negative test result.

Test Number:     21702

Date:     12/02/01

Result:

| | |
|---|---|
| Positive Control: | Positive |
| Negative Control: | Negative |
| Test Result: | Negative |
| Overall Result: | PASS |

Authorised by................................ECACC, Head of Quality.....5/3/01...... Date

62

| Applicant's or agent's file reference number | BN 35 PCT | International application No. |

INDICATIONS RELATING TO A DEPOSITED MICROORGANISM (PCT Rule 13bis)

A. The indications made below relate to the microorganism referred to in the description
on page ___5___, line ___24___.

B. IDENTIFICATION OF DEPOSIT     Further deposits are identified on an additional sheet ☐

Name of depositary institution ECACC
European Collection of Cell Cultures

Address of depositary institution *(including postal code and country)*
Centre for Applied Microbiology & Research
Salisbury
Wiltshire SP4 OJG, United Kingdom

| Date of deposit | Accession Number |
|---|---|
| August 30, 2000 | 00083008 |

C. ADDITIONAL INDICATIONS *(leave blank if not applicable)*     This information is continued on an additional sheet ☐

In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State.

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1992)

Centre for Applied Microbiology and Research
&
European Collection of Cell Cultures
This document certifies that Virus
(Deposit Ref. V00083008) has been accepted as a patent deposit,
in accordance with
The Budapest Treaty of 1977,
with the European Collection of Cell Cultures on 30$^{TH}$ August 2000
Dr P J Packer
Quality Manager, ECACC Form BP/4 (first page)

Appendix 3

Page 25

| IV. | CONDITIONS UNDER WHICH THE VIABILITY TEST HAS BEEN PERFORMED [4] |
|---|---|

V00083008 - MVA-BN

VIABILITY OF MVA-BN WAS TESTED BY GROWING THE VIRUS ON BHK CELLS AND CALCULATING THE TCD50.

| V. | INTERNATIONAL DEPOSITARY AUTHORITY | |
|---|---|---|
| Name: | Dr P J Packer | Signature(s) of person(s) having the power to represent the International Depositary Authority or of authorized official(s): |
| Address: | ECACC CAMR Porton Down Salisbury Wiltshire SP4 0JG | Date: 14/12/cv  [signature] |

[4] Fill in if the information has been requested and if the results of the test were negative.

APPENDIX 3

Page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

```
TO

BAVARIAN NORDIC RESEARCH                VIABILITY STATEMENT
INSTITUTE GMBH                          Issued pursant to Rule 10.2 by the
FRAUNHOFERSTRASSE 18B                   INTERNATIONAL DEPOSITARY AUTHORITY
D-82152 MARTINSRIED                     identified on the following page
GERMANY NAME AND ADDRESS OF THE PARTY
    TO WHOM THE VIABILITY OF STATEMENT
              IS ISSUED
```

| I.   DEPOSITOR | II.   IDENTIFICATION OF THE MICROORGANISM |
|---|---|
| Name:    BAVARIAN NORDIC RESEARCH<br>          INSTITUTE GMBH<br><br>Address:  FRAUNHOFERSTRASSE 18B<br>          D-82152 MARTINSRIED<br>          GERMANY | Accession number given by the<br>INTERNATIONAL DEPOSITORY AUTHORITY:<br><br>V00083008<br><br>Date of the deposit or of the transfer:<br>30$^{TH}$ August 2000 |

| II.   VIABILITY STATEMENT |
|---|
| The viability of the microorganism identified under II above was tested<br>on                                    [2]. On that date, the said microorganism was<br><br>[X] [3]    viable<br><br>[ ] [3]    no longer viable |

1   Indicate the date of the original deposit or, where a new deposit or a transfer has been made, the most relevant date (date of the new deposit or date of the transfer).

2   In the cases referred to in Rule 10.2 (a) (ii) and (iii), refer to the most recent viability test.

3   Mark with a cross the applicable box.

66

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

TO
BAVARIAN NORDIC RESEARCH
INSTITUTE GMBH
FRAUNHOFERSTRASSE 18B
D-82152 MARTINSRIED
GERMANY

NAME AND ADDRESS
OF DEPOSITOR

| I. IDENTIFICATION OF THE MICROORGANISM | |
|---|---|
| Identification reference given by the DEPOSITOR:<br><br>MVA-BN | Accession number given by the INTERNATIONAL DEPOSITARY AUTHORITY:<br><br>V00083008 |

II. SCIENTIFIC DESCRIPTION AND/OR PROPOSED TAXONOMIC DESIGNATION

The microorganism identified under I above was accompanied by:

[X] A scientific description

[ ] A proposed taxonomic designation (Mark with a cross where applicable)

III. RECEIPT AND ACCEPTANCE

This International Depository Authority accepts the microorganism identified under I above, which was received by it on 30TH August 2000 (date of the original deposit)¹

IV. RECEIPT OF REQUEST FOR CONVERSION

The microorganism identified under I above was received by this International
Depository Authority on            (date of the original deposit) and
A request to convert the original deposit to a deposit under the Budapest Treaty
was received by it on              (date of receipt of request for conversion)

IV. INTERNATIONAL DEPOSITORY AUTHORITY

| Name: Dr P J Packer | Signature(s) of person(s) having the power to represent the International Depository Authority or of authorized officials(s): |
|---|---|
| Address: ECACC<br>CAMR<br>Porton Down<br>Salisbury SP4 OJG | Date: |

Where Rule 6.4(d) applies, such date is the date on which the status of international depositary authority was acquired Form BP/4 (sole page)                                                           1991

TABLE 1

|  | CEF | Hela | HaCat | 143B | BHK | Vero | CV-1 |
|---|---|---|---|---|---|---|---|
| MVA-BN | 579.73 | 0.04 | 0.22 | 0.00 | 65.88 | 2.33 | 0.00 |
| MVA-575 | 796.53 | 0.15 | 1.17 | 0.02 | 131.22 | 10.66 | 0.06 |
| MVA-HLR | 86.68 | 124.97 | 59.09 | 0.83 | 87.86 | 34.97 | 29.70 |
| MVA-Vero | 251.89 | 27.41 | 1.28 | 2.91 | 702.77 | 1416.46 | 4.48 |

Virus amplification above the input level after 4 days infection
Amplification ratio = output $TCID_{50}$ - input $TCID_{50}$.
Values are in $TCID_{50}$.

What is claimed is:

1. A vaccinia virus which is that virus deposited at the European Collection of Cell Cultures (ECACC), Salisbury (UK) under number V00083008 and derivatives thereof.

2. The vaccinia virus of the claim 1, comprising at least one heterologous nucleic acid sequence.

3. The vaccinia virus of claim 2, wherein the heterologous nucleic acid sequence codes for at least one antigen, antigenic epitope, or a therapeutic compound.

4. A pharmaceutical composition comprising the vaccinia virus of claim 1 and pharmaceutically acceptable carrier, diluent and/or additive.

5. A vaccine comprising the vaccinia virus of claim 1.

6. A method for affecting a specific immune response in a living animal body, comprising administering an amount of a vaccinia preparation which includes an effective amount of a vaccinia virus of claim 1.

7. The method of claim 6, wherein a specific immune response is induced.

8. The method of claim 6, wherein the animal is a human.

9. The method of claim 8, wherein the human is immune compromised.

10. A method of claim 6, wherein the specific immune response is against an orthopox virus.

11. A method of claim 10, wherein the specific immune response is against smallpox.

12. A method of claim 6, wherein the specific immune response is against a HIV.

13. A method of claim 6, wherein the animal is immune compromised.

14. A method of claim 6, wherein the preparation is administered in therapeutically effective amounts in a first inoculation of "priming inoculation" and in a second inoculation or "boosting inoculation".

15. A method of claim 14, wherein the specific immune response is against an orthopox virus.

16. A method of claim 15, wherein the specific immune response is against smallpox.

17. A method of claim 14, wherein the specific immune response is against HIV.

18. A vaccinia virus of claim 3, wherein the heterologous nucleic acid codes for an HIV epitope.

19. A method for affecting an immune response against HIV in a living animal body, comprising administering an amount of a vaccinia preparation which includes an effective amount of a vaccinia virus of claim 18.

20. The method of claim 19, wherein a specific immune response is induced.

21. The method of claim 19, wherein the animal is a human.

22. A method for affecting a specific immune response in a living animal body, comprising administering an amount of a vaccinia preparation which includes an effective amount of a vaccinia virus of claim 18, wherein the preparation is administered in therapeutically effective amounts in a first inoculation or "priming inoculation" and in a second inoculation or "boosting inoculation".

23. The method of claim 22, wherein a specific immune response is induced.

24. The method of claim 22, wherein the animal is a human.

25. A method of claim 14 or 22, wherein the animal is immune compromised.

26. The method of claim 25, wherein the immune compromised animal is a human.

27. A method of affecting a specific immune response in a living animal body, comprising administering an amount of a vaccine preparation which includes an effective amount of a vaccinia virus of claim 1.

28. The method of claim 27, wherein a specific immune response is induced.

29. The method of claim 27, wherein the animal is a human.

30. A method of affecting a specific immune response in a living animal body, wherein a vaccine preparation which includes an effective amount of a vaccinia virus of claim 1 is administered in a first inoculation or "priming inoculation" and in a second incoculation or "boosting inoculation".

31. The method of claim 30, wherein a specific immune response is induced.

32. The method of claim 30, wherein the animal is a human.

33. A method of enhancing a specific immune response against an antigen, comprising including the virus of claim 1 as an adjuvant in an immunogenic composition.

34. A genome of the vaccinia virus of claim 1.

* * * * *

UNITED STATES PATENT AND TRADEMARK OFFICE
CERTIFICATE OF CORRECTION

PATENT NO. : 6,761,893 B2
DATED : July 13, 2004
INVENTOR(S) : Paul Chaplin et al.

It is certified that error appears in the above-identified patent and that said Letters Patent is hereby corrected as shown below:

Title page,
Item [75], Inventors, "Munich" should be -- Munchen --; and "Martinsried (DE)" should be -- Glen Waverly (AU)"
Item [56], References Cited, OTHER PUBLICATIONS, "Caroll, W.M. and Moss, B." reference, "1998-211" should be -- 198-211 --.

Column 5,
Line 25, "1988" should be -- 1998 --.

Column 16,
Line 40, "titrated" should be -- titred --.

Signed and Sealed this

Fifteenth Day of February, 2005

JON W. DUDAS
*Director of the United States Patent and Trademark Office*